United States Patent
Schultheiss et al.

(10) Patent No.: US 8,162,859 B2
(45) Date of Patent: Apr. 24, 2012

(54) SHOCK WAVE TREATMENT DEVICE AND METHOD OF USE

(75) Inventors: Reiner Schultheiss, Illighausen (CH); Wolfgang Schaden, Vienna (AT); John Warlick, Woodstock, GA (US); Robert Goeschl, Winzendorf (AT)

(73) Assignee: General Patent , LLC, Marietta, GA (US)

( * ) Notice: Subject to any disclaimer, the term of this patent is extended or adjusted under 35 U.S.C. 154(b) by 1423 days.

(21) Appl. No.: 11/422,388

(22) Filed: Jun. 6, 2006

(65) Prior Publication Data

US 2007/0016112 A1  Jan. 18, 2007

Related U.S. Application Data

(60) Provisional application No. 60/763,018, filed on Jan. 27, 2006, provisional application No. 60/688,927, filed on Jun. 9, 2005.

(51) Int. Cl.
*A61N 7/00* (2006.01)

(52) U.S. Cl. .......................................................... 601/2

(58) Field of Classification Search ................ 601/2–4; 600/439; 606/1, 7, 127–128
See application file for complete search history.

(56) References Cited

U.S. PATENT DOCUMENTS

| | | | |
|---|---|---|---|
| 3,951,140 A | | 4/1976 | Eggleton et al. |
| 4,326,155 A | * | 4/1982 | Griebeler ...................... 318/576 |
| 4,593,699 A | * | 6/1986 | Poncy et al. .................. 600/459 |
| 4,638,800 A | * | 1/1987 | Michel ............................ 606/14 |
| 4,817,616 A | * | 4/1989 | Goldstein ...................... 600/463 |
| 4,940,050 A | * | 7/1990 | Forssmann et al. ............... 601/4 |
| 5,240,002 A | * | 8/1993 | Brisson et al. ................ 600/439 |
| 5,409,002 A | * | 4/1995 | Pell ............................... 600/407 |
| 5,524,620 A | * | 6/1996 | Rosenschein ................ 600/407 |
| 5,703,922 A | * | 12/1997 | Rattner ............................ 378/65 |
| 5,748,563 A | * | 5/1998 | Hofmann ...................... 367/147 |
| 5,800,365 A | * | 9/1998 | Zhong et al. ...................... 601/4 |
| 5,813,409 A | * | 9/1998 | Leahy et al. .................. 128/897 |
| 5,836,905 A | * | 11/1998 | Lemelson et al. .............. 604/21 |
| 5,941,838 A | * | 8/1999 | Eizenhofer ....................... 601/2 |
| 5,999,847 A | * | 12/1999 | Elstrom ......................... 604/20 |
| 6,113,560 A | | 9/2000 | Simnacher |

(Continued)

FOREIGN PATENT DOCUMENTS

| | | |
|---|---|---|
| EP | 1 254 638 | 5/2000 |
| JP | 2002-085418 | 3/2002 |
| JP | 2004-215862 | 8/2004 |

OTHER PUBLICATIONS

R.Meirer, et al; Extracorporal shock wave may enhance skin flap survival in an animal model; British Journal of Plastic Surgery; vol. 58, Issue 1, Jan. 2005, pp. 53-57; Copyright 2004; The British Association of Plastic Surgeons, published by Elsevier Ltd.

(Continued)

*Primary Examiner* — Francis Jaworski
(74) *Attorney, Agent, or Firm* — David L King

(57) ABSTRACT

The system for treating an internal organ has a generator source for producing a shock wave connected to a portable shock wave applicator device, wherein the shock wave applicator device has a side-firing shock wave head having a variable angle adjustment relative to a release and lock connected handle or holder means for holding said device. The inclination of the shock wave head can be set to a fixed inclination to reach the organ at various locations or surfaces or can be pivotally inclined continuous to vary the treatment surfaces area.

20 Claims, 17 Drawing Sheets

U.S. PATENT DOCUMENTS

| | | | |
|---|---|---|---|
| 6,186,963 B1* | 2/2001 | Schwarze et al. | 601/2 |
| 6,217,531 B1* | 4/2001 | Reitmajer | 601/4 |
| 6,231,529 B1* | 5/2001 | Bauer et al. | 601/4 |
| 6,319,261 B1* | 11/2001 | Bowers | 606/127 |
| 6,390,995 B1 | 5/2002 | Ogden et al. | |
| 6,413,230 B1 | 7/2002 | Haupt et al. | |
| 6,428,531 B1 | 8/2002 | Visuri et al. | |
| 6,440,061 B1* | 8/2002 | Wenner et al. | 600/114 |
| 6,508,816 B2* | 1/2003 | Shadduck | 606/34 |
| 6,551,308 B1* | 4/2003 | Muller et al. | 606/10 |
| 6,554,824 B2 | 4/2003 | Davenport et al. | |
| 6,663,594 B2* | 12/2003 | Sahatjian et al. | 604/113 |
| 6,755,821 B1 | 6/2004 | Fry | |
| 7,305,264 B2* | 12/2007 | Larson et al. | 600/427 |
| 7,520,856 B2* | 4/2009 | Vaezy et al. | 600/439 |
| 7,553,284 B2* | 6/2009 | Vaitekunas | 600/439 |
| 7,601,127 B2* | 10/2009 | Schultheiss et al. | 601/2 |
| 2004/0167445 A1 | 8/2004 | Simnacher | |
| 2005/0021013 A1 | 1/2005 | Visuri et al. | |
| 2006/0051328 A1 | 3/2006 | Johnson | |
| 2010/0036294 A1* | 2/2010 | Mantell et al. | 601/4 |

OTHER PUBLICATIONS

T. Nishida, et al: Extracorporeal Cardiac Shock Wave Therapy Markedly Ameliorates Ischemia-Induced Myocardial Dysfunction in Pigs in Vivo; Circulation; Nov. 9, 2004; *Circulation*. 2004; 110; pp. 3055-3061.

L.Gerdesmeyer, et al; Antibacterial Effects of Extracorporeal Shock Waves; World Fed for Ultrasound in Medicine & Biology;printed USA;Elsevier, vol. 31,No. 1, pp. 115-119, 2005.

G.Haupt, et al; Effect of Shock Waves on the Healing of Partial-Thickness Wounds in Piglets; Journal of Surgical Research, vol. 49, No. 1, pp. 45-48, Jul. 1990, Copyright 1990 by Academic Press, Inc.

Jagadeesh, G. et al;"Novel applications of micro-shock waves in biological sciences", J. Indian Inst. Sci. 2002, 82, pp. 1-10.

Thiel, M. et al; "The use of shock waves in medicine—a tool of the modem OR; an overview of basic physical principles, history and research", Min Invas Ther & Allied Technol 2000; 9(3/4) 247-253.

Huemer, Georg M. et al; "Comparison of the effectiveness of gene therapy with transforming growth factor-B or extracorporal shock wave therapy to reduce ischemic necrosis in an epigastric skin flap model in rats"; From the Clinical Department of Plastic and Reconstructive Surgery, Cardiac Surgery, Orthopedics, and the Ludwig-Boltzmann Institute for Quality Control in Plastic Surgery, Medical University Innsbruck Austria; Feb. 13, 2004; copyright 2005 by the Wound Healing Society. ISSN: 1067-1927 (Wound Rep Reg 2005; 13:262-268).

* cited by examiner

SHOCK WAVE TREATMENT DEVICE AND METHOD OF USE

RELATED APPLICATIONS

This application is a continuation in part and claims priority to U.S. Provisional Application No. 60/763,018 filed on Jan. 27, 2006 entitled "Shock Wave Treatment and Method of Use" and also claims priority to U.S. 60/688,927 filed on Jun. 9, 2005 entitled "Pressure Pulse/Shock Wave Therapy Methods for Organs" and to U.S. Ser. No. 11/238,731 filed on Sep. 29, 2005 entitled "Pressure Pulse/Shock Wave Therapy Methods for Organs".

FIELD OF THE INVENTION

The present invention relates to a method and a device for generating shock waves generally, more specifically to a method and device for treating internal organs or tissue.

BACKGROUND OF THE INVENTION

The use of shock waves to treat various conditions affecting the bone or soft tissues of a mammal, usually a human is known.

Shock waves produce a high energy pulse that when focused can pulverize hard calcium deposits such as kidney stones. This technology is commonly and very successfully employed in lithotripsy.

More recently, the use of shock waves has been employed in the art of healing non union bone fractures and in treating soft tissues and organs extracorporeally in a non-invasive manner.

The pressure pulse or wave form when applied was thought to require a high energy to achieve a deep penetration to an affected organ, as a result focused beams were transmitted that had a focal point or region set at a distance deep enough to penetrate the underlying organ or tissue. It was believed that the skeletal system of hard bone mass greatly dampened the wave pattern making it difficult to treat such organs as the heart.

In U.S. Pat. No. 6,755,821 B1 entitled "A System and Method for Stimulation and/or Enhancement of Myocardial Angiogenesis" a proposed solution to treating the heart using shock waves was proposed. Shock-waves were applied using a combination lithotripsy probe/balloon system, comprising a needle and cannular balloon which can be inserted through the skin at a point between the ribs into the cavity beneath the chest wall and overlying the heart. Alternatively, the shock-wave can be administered extracorporeally or via a catheter. A fluid injector was connected to the balloon, allowing it to be inflated with saline or other appropriate fluid to fill the space (for transmission of shock waves and/or to displace tissue—such as lung) and contact the surface of the heart. A shock-wave (acoustic) generator was used to generate shock-waves through the lithotripsy probe, through the fluid and into the myocardial tissue. The fluid provides a uniform medium for transmission of the acoustic energy, allowing precise focus and direction of the shock-wave to induce repeatable cavitation events, producing small fissures which are created by the cavitation bubbles. In this case, channels would not be 'drilled' into the heart muscle, minimizing trauma to the tissue while still creating conditions that will stimulate increased expression of angiogenic growth factors.

The concept in U.S. Pat. No. 6,755,821 provides an alternative to procedures in place today that rely on lasers. As stated in the above referenced patent.

"Transmyocardial revascularization (TMR) using a laser (sometimes referred to as TMLR, LTMR, PMR, PTMR, or DMR) has been developed over the past decade, initially by a company called PLC Systems, Inc., of Franklin, Mass. PLC's system utilizes a high power (800-1000 W) carbon dioxide ($CO_2$) laser which drills small channels in the outside (epicardial) surface of the myocardium in a surgical procedure. The holes communicate with the left ventricle, which delivers blood directly to the heart muscle, mimicking the reptilian heart. Many other companies are developing laser TMR systems, most introducing the laser light via optical fibers through a flexible catheter, making the procedure less-invasive. These companies include Eclipse Surgical Technologies, Inc., of Sunnyvale, Calif., and Helionetics, Inc., of Van Nuys, Calif. The Eclipse TMR system uses a Ho:YAG laser with a catheter-delivered fiber optic probe for contact delivery to the myocardium. The Helionetics system is based on an excimer laser. In addition to the holmium:YAG and excimer lasers, and other types of lasers have been proposed for TMR.

While the channels created during TMR are known to close within 2-4 weeks, most patients tend to improve clinically over a period of 2-6 months.

Such clinical improvement may be demonstrated by reduction in chest pain ("angina"), and a dramatic increase in exercise tolerance ("ETT", or treadmill test). The mechanism of laser TMR is not fully understood, but it is postulated that the laser causes near-term relief of angina through denervation or patent channels, with subsequent long-term clinical improvement due to angiogenesis, i.e., growth of new blood vessels, mainly capillaries, which perfuse the heart muscle. These new "collateral" vessels enable blood to reach downstream ("distal") ischemic tissues, despite blockages in the coronary arteries. Some of the possible mechanisms by which the laser induces angiogenesis could include activation of growth factors by light, thermal, mechanical, cavitational or shockwave means. In fact, all lasers which have been successfully used for TMR are pulsed systems, and are known to create shock waves in tissue, and resulting cavitation effects."

The problem of delivery of a shock wave to an internal organ is more complex than simply avoiding bone tissue. In the case of treating the heart special care must be taken to avoid damaging the thin membrane of the nearby lung. Shock waves inadvertently transmitted to this area can cause bleeding and other damage.

Another problem for the use of shock waves is internal organs are three dimensional masses that in the case of the heart need the waves to be directed from two sides front and back, more preferably from at least three directions.

Accordingly the devices such as the laser or the shock wave system of U.S. Pat. No. 6,755,821 are limited to one surface of the heart or would require multiple points of entry.

The team of inventors of the present invention has developed both a device and a methodology for treating an internal organ which addresses these limitations and provides a multiple direction system for delivering shock waves.

SUMMARY OF THE INVENTION

The system for treating an internal organ has a generator source for producing a shock wave connected to a handheld or otherwise small shock wave applicator device, wherein the shock wave applicator device has a side-firing shock wave head having a variable angle adjustment relative to a release and lock connected handle or holder means for holding said device. The inclination of the shock wave head can be set to a fixed inclination to reach the organ at various locations or surfaces or can be pivotally inclined continuous to vary the treatment surface area.

The pulse or wave propagation being emitted from the head on a sideways direction relative to the holder means enables the surgeon to rotate the head about a longitudinal axis of the holder or tilt the head relative to the length of the holder providing an infinite number of angular choices for emitting the wave pattern. The device may employ acoustic shock waves from electromagnetic or piezo electric, ballistic or electro hydraulic sources or generators.

In a preferred embodiment the head portion or end includes two electrodes or two tips in one assembly of an electrode as is described in U.S. Pat. No. 6,217,531 and is commercially available under the trade name Smarttrode to create a shock wave generating spark, and the head portion further includes a reflector for redirecting and shaping the wave pattern. The head is preferably round or oval of a small geometric size sufficient to be positioned under or around the soft tissue of an organ to permit access around the periphery of the organ being treated. Alternatively the reflector and head of the applicator can be an oval of more ellipsoidal shape with the major axis lying along the longitudinal axis of the device. In such a case the minor diameter transverse to the longitudinal axis can be made 3 cm or preferably 2 cm or less. The device can further include an integral shielding means which would insure the only emitted shockwave energy was directed outward from the front cover or membrane of the shock wave head. The shielding means preferably would be an air cushion covering at least the back and preferably the sides of the applicator head to dissipate any transmitted energy. This is particularly useful to prevent damage to the thin lung membrane during an open heart procedure. Alternatively the shielding means can be made a part of a sterile sleeve or even a separate sterile layer positioned between the treated heart and the underlying lung. In one embodiment the device is disposable intended for one time use.

The applicator device may be used by placing it inside a disposable sterile sleeve or cover. In such a case the applicator can be simply cleaned with a disinfecting agent prior to use as it is not directly exposed to the tissue. Alternatively the applicator without a sleeve or cover can be used wherein the applicator should be sterilized prior to use. In either use the sleeve or cover or the applicator without a cover should be coupled acoustically to the treated tissue or organ by a sterile coupling fluid or viscous gel like ultrasound gels or even NaCl solution to avoid transmission loss.

The method of employing the shock wave applicator device comprises the steps of providing an at least partially exposed or direct access portal to an organ, activating an acoustic shock wave generator or source to emit acoustic shock waves from a shock wave applicator head of a shock wave applicator; and subjecting the organ to the acoustic shock waves stimulating said organ wherein the organ is positioned within an unobstructed path of the emitted shock waves, positioning the shock wave head adjacent to and on an inclination relative to the organ, firing the electrodes and emitting a shock wave pattern in a generally transverse direction relative to the applicator. The method further comprises repositioning the shock wave head at a second position or inclination and firing the electrode. The step of positioning the applicator may further include setting a holding means at an angle between 0° and about 360° more typically between 0° and 180° relative to the applicator prior the firing the electrodes, the holder means being a pivotable handle. In one embodiment the emitted shock waves are divergent or near planar. In another embodiment the emitted shock waves are convergent having a geometric focal volume or focal point at a distance of at least X from the source, the method further comprising positioning the organ at a distance at or less than the distance X from the source. The organ is a tissue having cells. The tissue can be an organ of a mammal. The mammal may be a human or an animal. The organ may be a heart, a brain, a liver or a kidney or any other organ with associated other types of tissue. The tissue may be a part of the vascular system, a part of the nervous system, a part of the urinary or reproductive system.

The method of stimulating an organ can further include a result wherein the step of subjecting the organ to acoustic shock waves stimulates at least some of said cells within said organ to release or produce one or more of nitric oxygen (NO), vessel endothelial growth factor (VEGF), bone morphogenetic protein (BMP) or other growth factors.

The organ can be a tissue having a pathological condition, a tissue having been subjected to a prior trauma, a tissue having been subjected to an operative procedure, or a tissue in a degenerative condition. The organ is at least partially surgically exposed if not removed from the patient during the exposure to an unobstructed shock wave treatment.

The method may further include the steps as activating the applicator device to transmit the shock wave pulses in response to a repetitive body or organ function. In particular the method may include triggering the shock wave pulse during the R phase of the QRS and T curve or the contraction of a heart wherein the R phase is that portion of the heartbeat depicted by and including the peak amplitude on an ECG monitored display. This controlled pulse triggering avoids irregular heartbeat patterns from being stimulated by the transmission of the shockwave pulses.

DEFINITIONS

"cirrhosis" liver disease characterized pathologically by loss of the normal microscopic lobular architecture, with fibrosis and nodular regeneration. The term is sometimes used to refer to chronic interstitial inflammation of any organ.

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"extracorporeal" occurring or generated outside the living body.

A "generalized paraboloid" according to the present invention is also a three-dimensional bowl. In two dimensions (in Cartesian coordinates, x and y) the formula $y''=2px$ [with n being $\neq 2$, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p(−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

"myocardial infarction" infarction of the myocardium that results typically from coronary occlusion, that may be marked by sudden chest pain, shortness of breath, nausea and loss of consciousness, and that sometimes results in death.

"open heart" of, relating to, or performed on a heart which could be temporarily relieved of circulatory function and surgically opened for inspection and treatment.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100 ns. The duration of a shock wave is typically below 1-3 micro-seconds (μs) for the positive part of a cycle and typically above some micro-seconds for the negative part of a cycle.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

Figure 1:
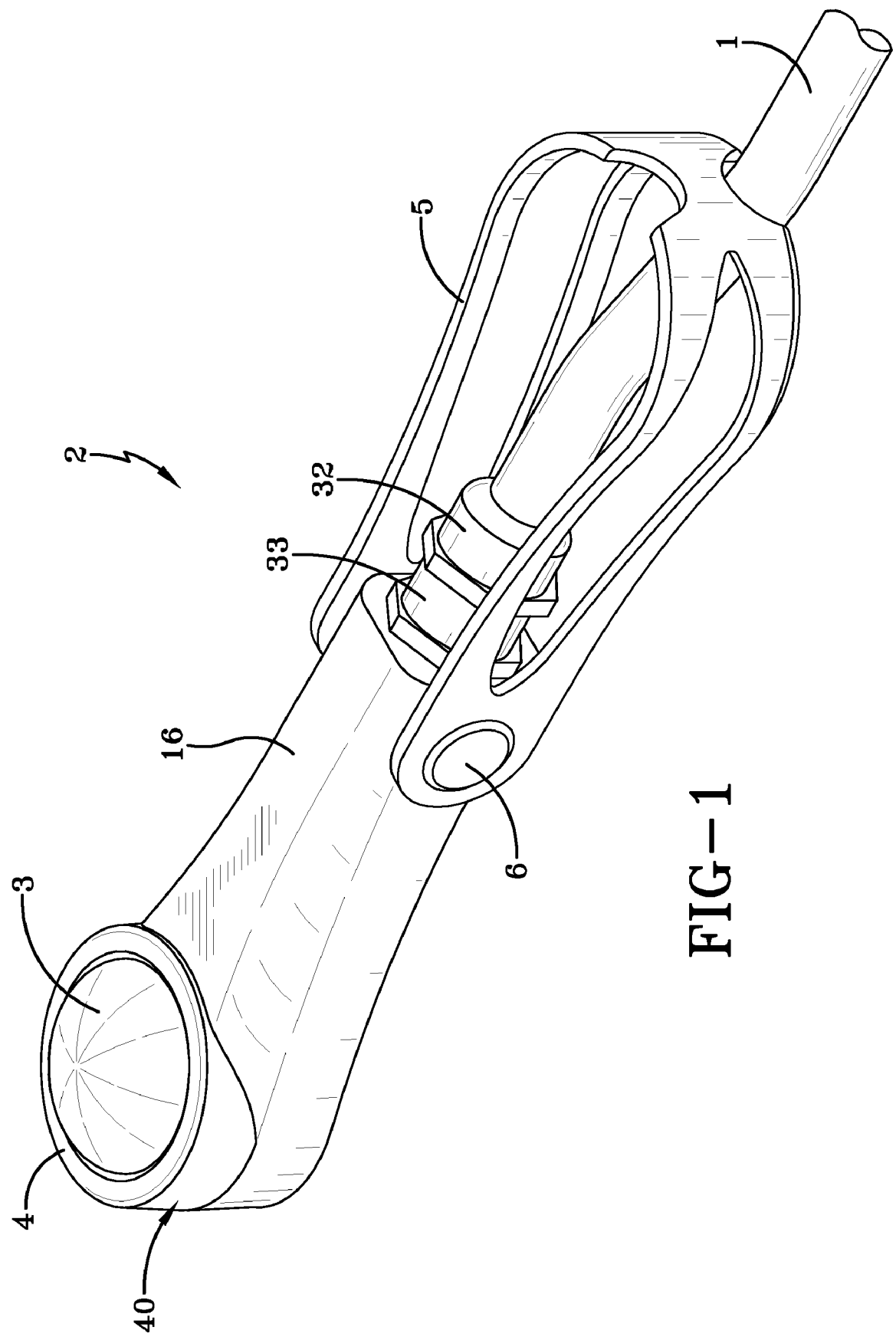
FIG. 1 is a perspective view of the shock wave applicator according to the present invention.
Figure 2:
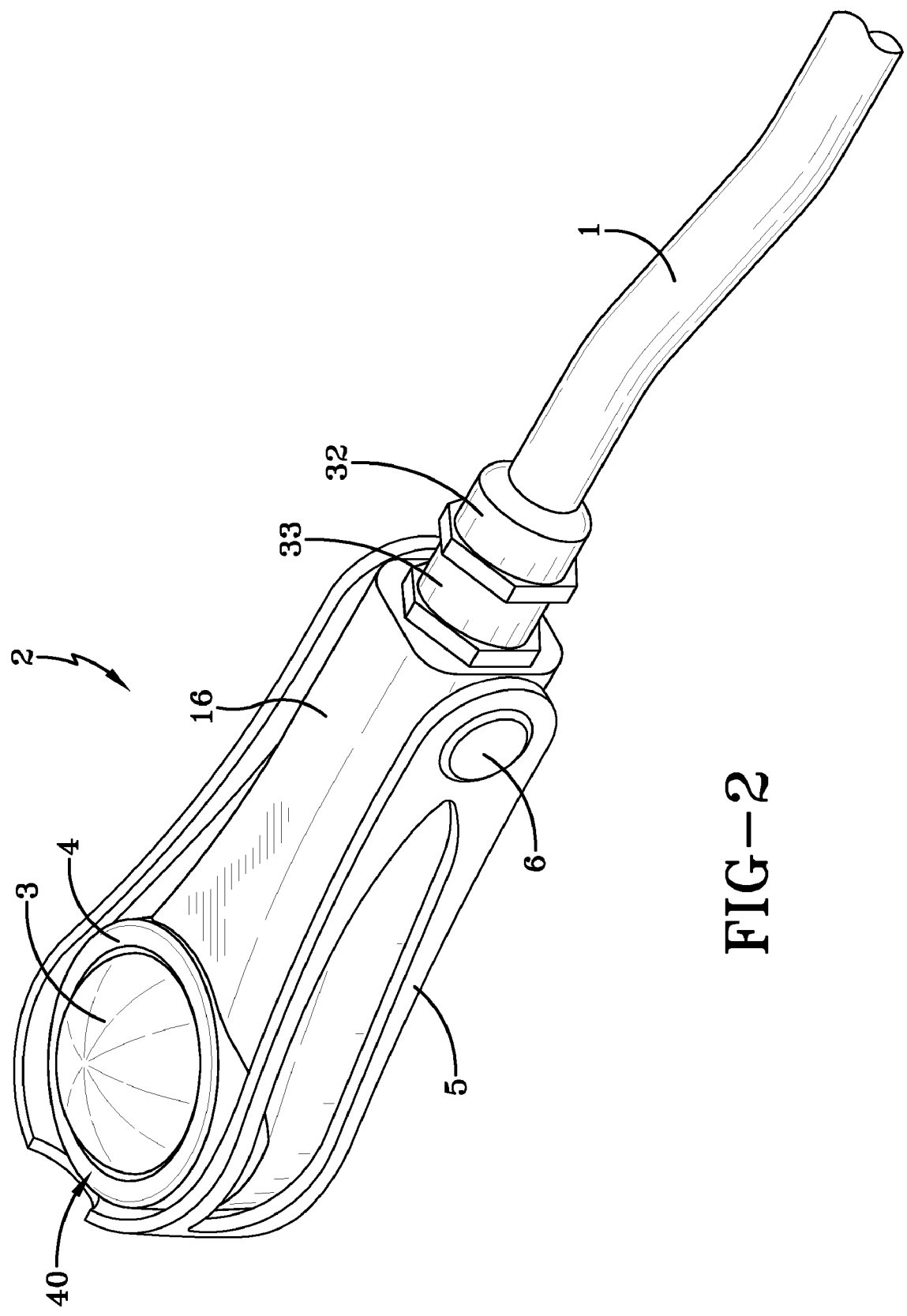
FIG. 2 is a second perspective view showing the pivotable handle rotated 180° toward the shock wave head end of the device.

With reference to FIGS. 1 and 2 a small portable hand-held shock wave applicator device 2 is illustrated. The shock wave applicator 2 has a cable 1 extending from an end of an applicator housing 16. The cable 1 is connected to a shock wave generator (schematically illustrated in FIG. 12) and as illustrated in FIGS. 1 and 2 fastened to the applicator housing 16 via a pair of threaded connectors 32, 33.

At the opposite end of the applicator 2 is an applicator head portion 40 as shown the applicator head portion 40 has a rounded contour with a diameter of approximately 5 cm, preferably smaller which enables the device to be easily positioned around or under the organ to be treated. It is in this portion 40 that the shock wave patterns are produced, reflected and emitted to the organ or tissue 100 being treated. The head portion 40 includes an outer membrane 3 which is sealed and retained by the annular fixation ring 4 which secures and holds the membrane 3.

Attached to the applicator housing 16 is an external pivotable handle 5 which can be swiveled about a lock and release pin 6. Preferably the handle 5 can be moved and fixed in position at various inclinations. In the illustrated embodiment the handle 5 is shown being movable in a range of 0° to 180° or more as much as 360° as can be seen in FIG. 1 compared to FIG. 2. In use the handle can be fixed at any inclination so desired preferably between 0° and 180° as shown. In use the surgeon can grasp the handle 5 squeezing it to release the locking mechanism and pre-orient it relative to the applicator head portion 40 and then simply position the head portion 40 relative to the organ by manipulating the handle 5. This feature is very useful when positioning the device under the heart or any other organ being treated that is partially exposed in the patient as a result of a surgical procedure.

Figure 5:
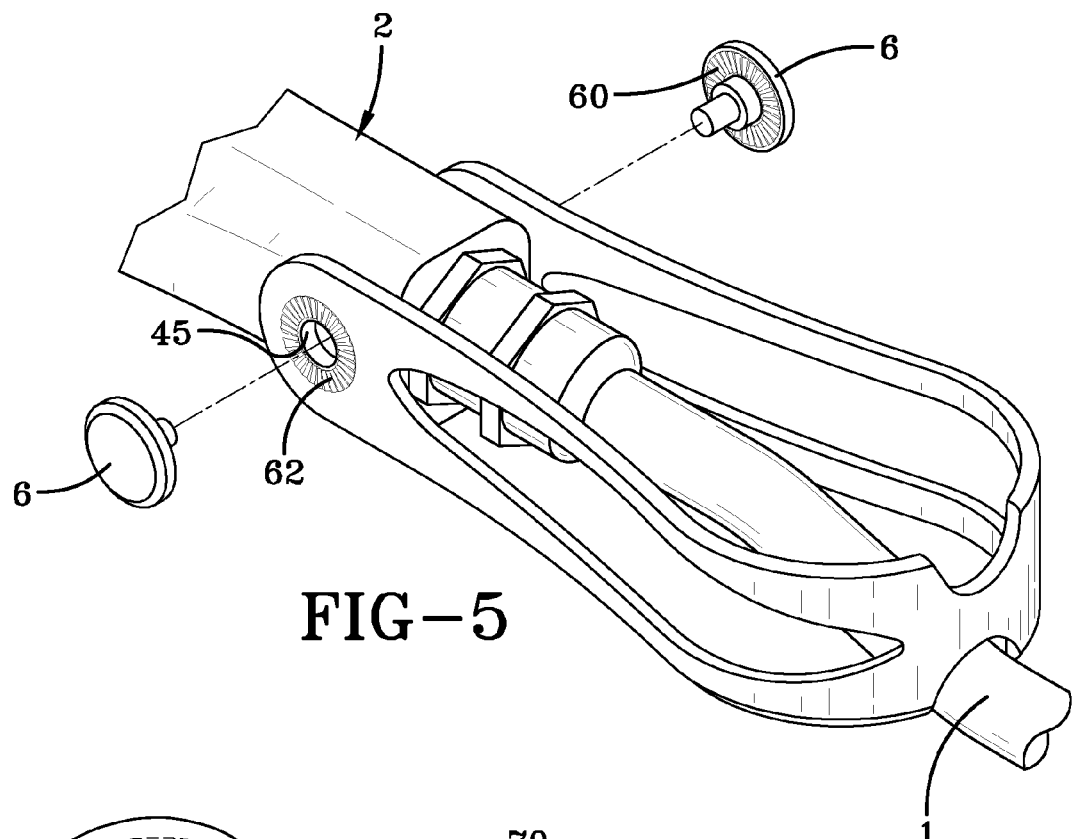
FIG. 5 is an exploded view of a portion of the handle and the pivot pin according to one embodiment of the invention.

With reference to FIG. 5 the pivotable handle 5 is shown attached to the pin 6 which has splines 60 providing an angular lock and release feature. The pivot hole 45 on the handle 5 has matching splines 62 and as the surgeon squeezes the handle the spline 60 disengages and the handle 5 can be rotated freely. By releasing pressure the splines 60, 62 re-engage due to the spring like "u" shaped handle 5 pushing against the pin 6. This feature provides a simple yet secure means for setting and releasing the handle 5 at a variety of inclinations.

Figure 3:
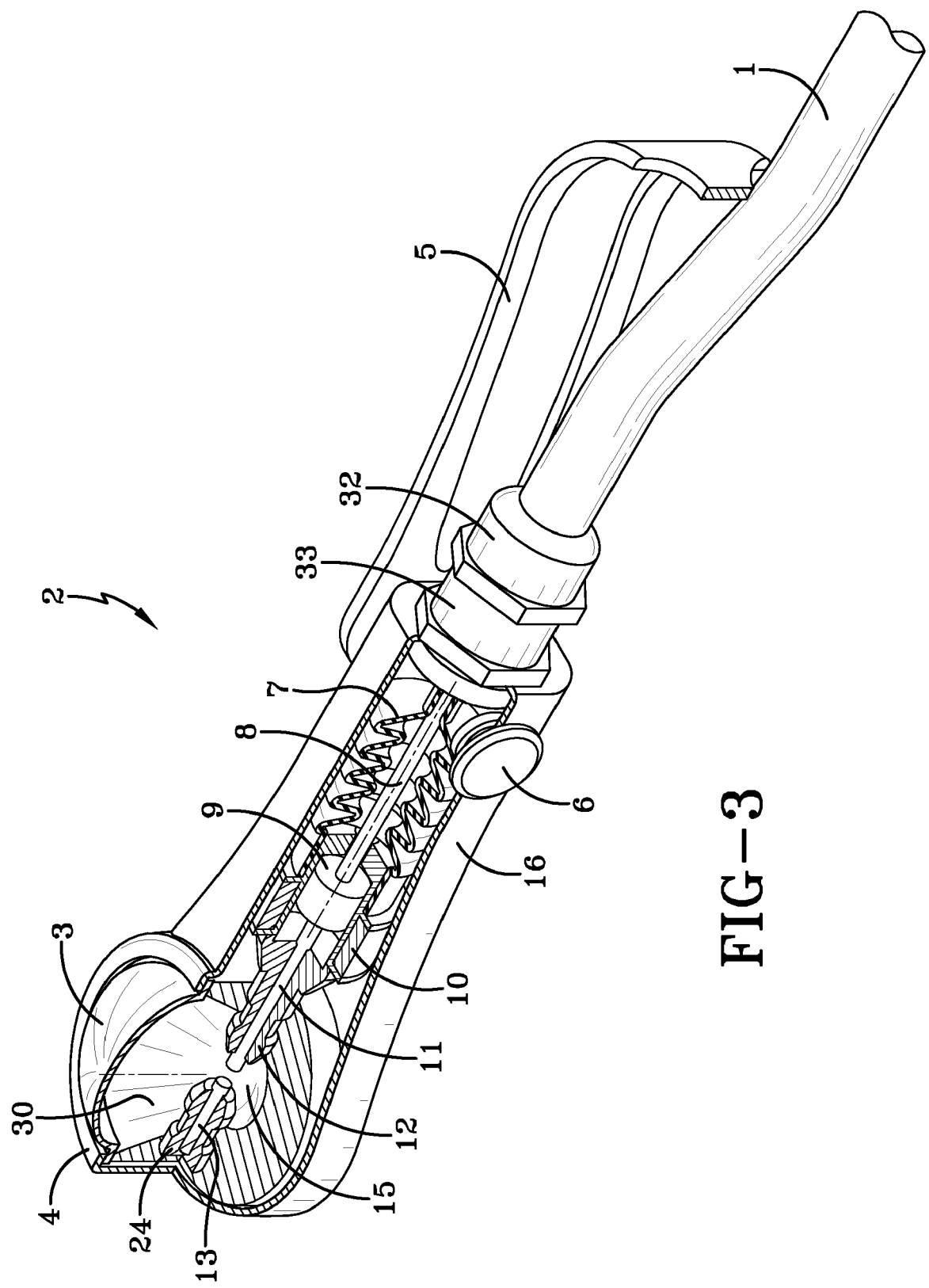
FIG. 3 is a third perspective view with a portion of the housing and handle removed exposing the internal components.
Figure 4:
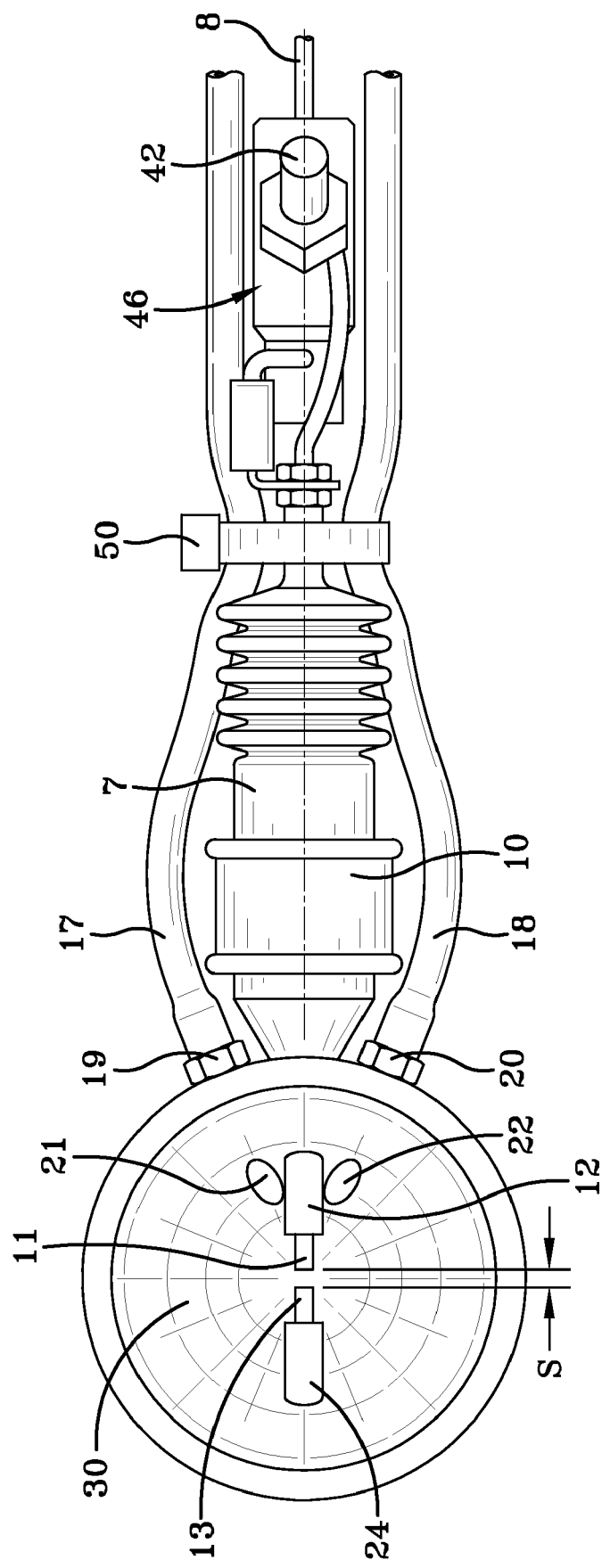
FIG. 4 is a plan view of the shock wave applicator internal components with the external housing and handle removed.

With reference to FIG. 3 a cross sectional view of the shock wave applicator device 2 is shown exposing the internal components. Passing through the cable 1 is a high voltage cable or rod 8 surrounded by an elastomeric insulation bellows 7. Encircling the rod 8 is a magnet 9 and a coil 10 for moving the magnet 9. At a distal end of the coil 10 is an insulator inner probe housing 12 for centering and holding an inner probe tip or electrode 11. At an opposite side of the applicator head portion 40 is an outer tip or electrode 13 embedded in an outer insulator housing 24. As shown in FIG. 4 the tips 11, 13 are aligned and gapped at a distance S to facilitate a spark gap which creates the shock wave when energized. Referring back to FIG. 3, partially surrounding the tips 11, 13 is a metal reflector 15. The reflector 15 opens to the membrane 3 and the internal surface provides the shape of the emitted wave patterns as a function of its geometric shape. The reflector 15 can be made of a numerous variety of shapes to achieve a desired wave pattern as will be discussed later in detail.

A cavity 30 is formed between the membrane 3 and the reflector 15 is filled with a fluid medium preferably filled with water. The water helps create a cavitation bubble when the spark is generated from which a shock wave 200 is propagated outward to the tissue or organ 100 to be treated.

It is possible to reduce the size of the applicator head 40 from about 5 cm maximum to much smaller almost half that size by reducing the volume in the cavity 30 and the size of the reflector 15. This can be accomplished by applying over pressure to the volume around the tips of the electrode to control the size of the emitted shock wave bubble. The size of the bubble will increase with the energy and this over pressure put on the tips of the electrode enable the wave propagation to be effectively the same as in the larger sized reflector head.

With reference to FIG. 4 the shock wave applicator 2 is shown with the housing 16 and handle 5 removed. As shown there are two water hoses illustrated, one water hose 17 is an inlet or supply hose 17 which is attached to the reflector 15 of the applicator head by a connector 19. Water from the inlet hose 17 can be pumped into the reflector cavity 30 through inlet holes or passageways 21. Water from the reflector cavity 30 can be removed via outlet holes or passageways 22 and sent back through the cable 1 by way of the outlet hose 18 which is connected to the reflector 15 by the connector 20. As shown the two hoses 17, 18 can be snugly secured on each side of the insulator bellows 7 by a strap 50.

As further shown the activation of the shock wave head 40 can be triggered by the surgeon by depressing the switch button 42 which closes the switch 46 allowing the high voltage current to pass along the cable or rod 8. Preferably this switch 46 including the switch button 42 is sealed within the housing 16 and the housing 16 can be squeezed to depress the switch button 42. This minimizes the protruding portions on the device 2 which is important to avoid damaging vessels or nerves on insertion of the device 2 into the access portal provided by the surgical procedure. The switch 46 could also be replaced with a foot switch or a switch attached to the power and control unit 41.

When treating an organ such as the heart the transmission of the shock waves can be triggered such that the shockwave pulse is emitted at a time when the heart is contracting. As is well known and observed in electro cardio graphs, ECG's, the heart transmits a repetitive beat or wave form often described as the QRS and T wave. The R portion of the curves includes the peak of the curve and it occurs during a heart contraction and during the contraction the heart is in a vironlevel phase such that the heart beat pattern cannot be altered during a triggering of the shockwave pulse. Accordingly it is preferred in sensitive patients that the shockwaves are transmitted during the R phase of QRS and T curves. To stimulate at other times during the heartbeat can create an alteration of the repetitive pattern of the heartbeat and could trigger an irregular and uncontrolled heart spasm which can easily be avoided by timing the shockwave pulse transmission to occur during the R curve portion of the heartbeat wave pattern. This method of controlling the transmission of the shockwave pulse can be tied to any number of repetitive body functions including, but not limited to pulse rate, pulmonary rate, breathing, brain wave activity or the like. The use of equipment monitoring devices to measure such body function can therefore be computer controlled to provide the necessary feedback to permit precise control of the triggering of the generator or shock wave source to insure a fully automated system wherein the temporal firing of the device is controlled without the need of the surgeon or physician intervention. A similar type technique of using the cardiac rhythm or pulse rate frequency of the patient was taught in U.S. Pat. No. 5,313,954 to control the shockwave frequency of generation and the subject matter of that patent is being incorporated by reference herein in its entirety. The advantage of such a technique is that it enables the determination of the frequency of extrasystoles such that the pulse generator can be deactivated for a given period of time to permit the patients circulation to regenerate itself during this interval. To do otherwise could induce irregular heart rates which in patients with weakened or damaged hearts is more problematic and potentially could be life threatening during the procedure of treatment. Accordingly in the case of treating the heart, in particular, such as the use of ECG gating to control the transmission or triggering of the shockwave pulse and the frequency of the pulse and the frequency of the pulse interval and dwell time between pulses is considered particularly important.

As shown the electrode tips 11, 13 spacing can be controlled by using the magnet 9 and the coil 10 which can move the inner tip 11 to control the gap spacing (S). Alternatively the tips 11, 13 can be replaced with adjustable electrodes using other means such as piezo ceramics, magnets, motors with gear boxes, pneumatic or hydraulic to change the tip distance.

A low cost alternative is to provide two fixed electrodes 11, 13 which are pre-set at fixed gaps and are not adjustable. In this way the entire device can be disposable adapted for a one procedure use which would provide the surgeon with a shock wave applicator device 2 capable to treat a single patient after which the device 2 can be simply discarded. This is possible due to the very low cost such a non-adjustable device 2 would require to manufacture. It is believed such a simple device may be usable for up to 4 or more treatments prior to being rendered inefficient due to the burning of the electrode tips. Alternatively any of the devices 2 can be easily refurbished by replacing worn components generally by replacing the firing mechanisms such as the electrode or tips.

In practice the use of the device 2 can be enhanced by the addition of a light and or miniature camera system (not shown) integrally attached at the head portion 40 or housing 16 of the applicator 2. The camera or light can be internal of the housing 16 and the housing can be or have a clear window portion for transmission. Preferably the light source is one or more LED's adapted for high light and low heat generation. The light and or viewing system combination can be connected to a remote optical monitor to enable the physician to focus on the rear of the organ being treated or any portion obstructed from view. Alternatively the surgeon may employ a flexible endoscope device to get light and a camera for viewing the treatment location and positioning the device 2.

Figure 18:
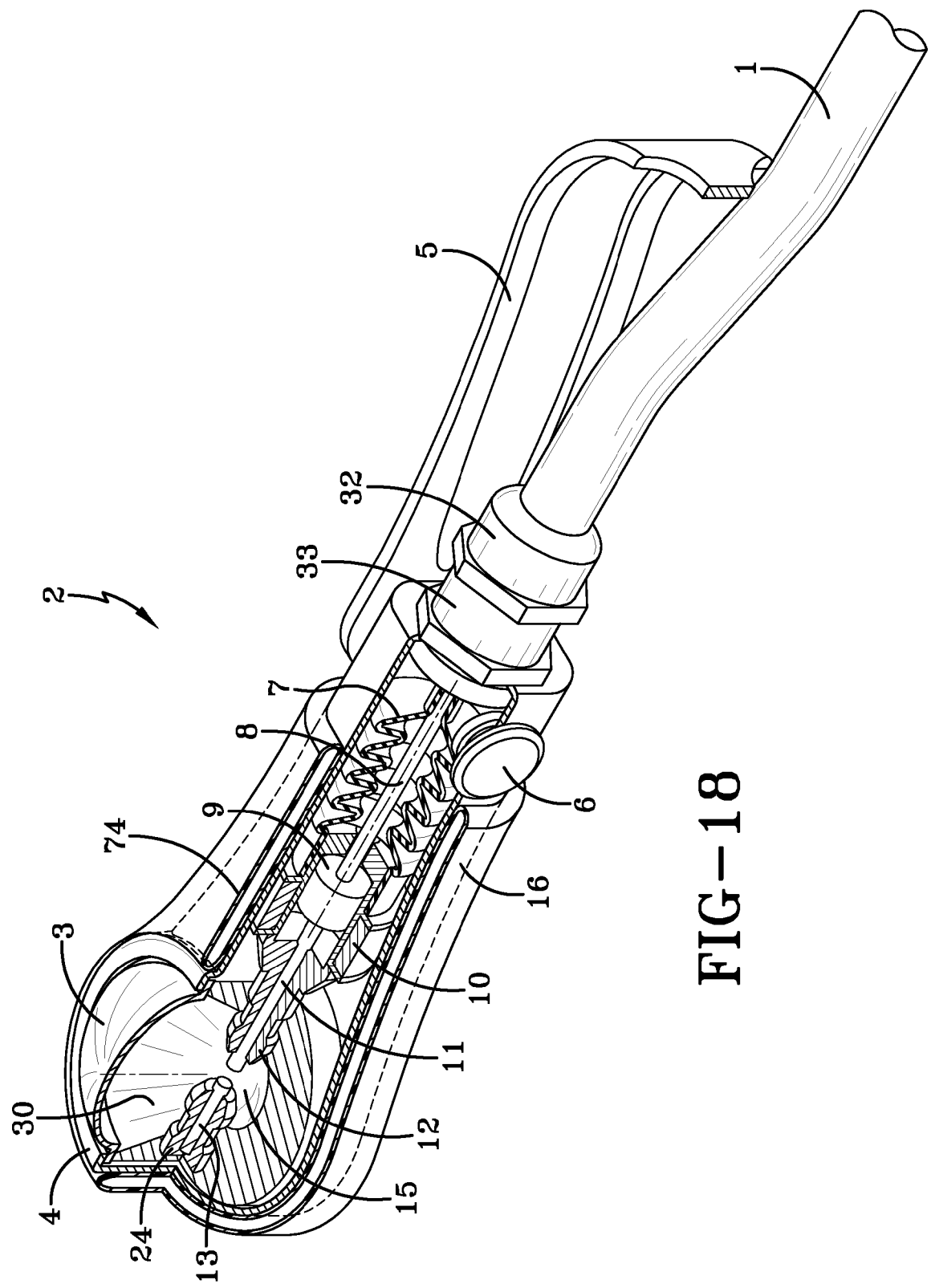
FIG. 18 is a cross sectional view of an applicator with an integral shielding means.
Figure 19:
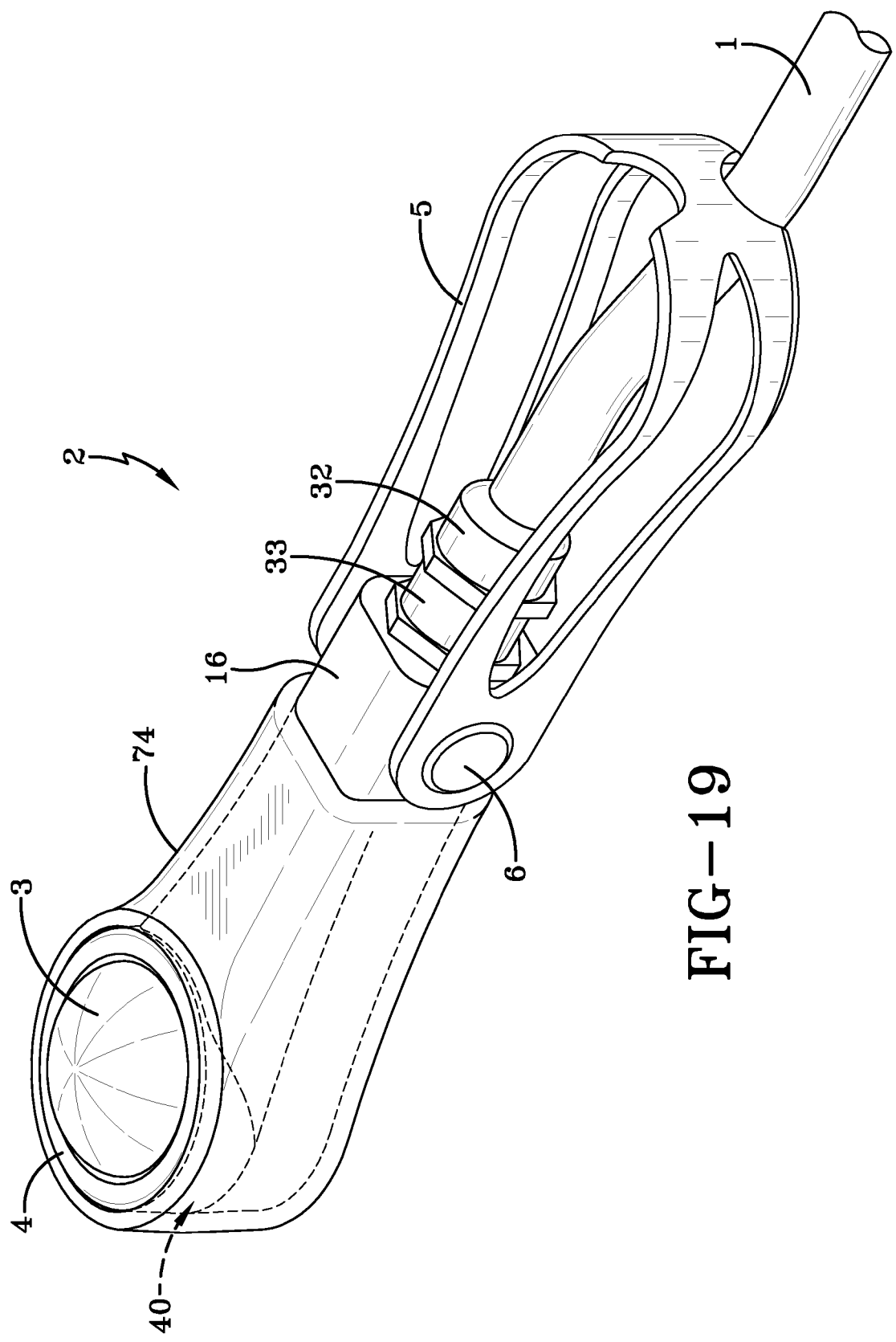
FIG. 19 is a view of the shielded applicator of FIG. 18.
Figure 20:
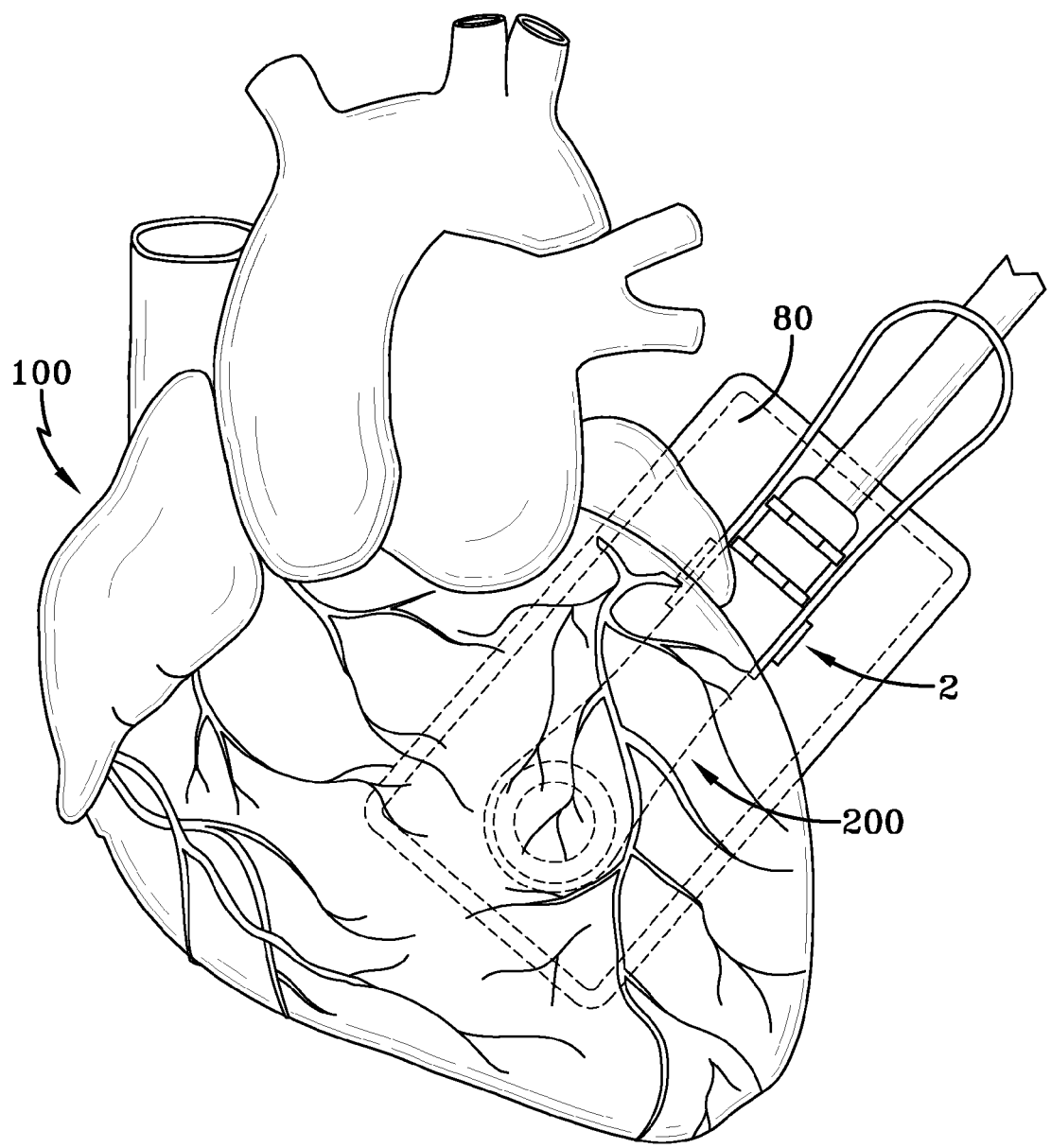
FIG. 20 is a separate shielding means for use with the device of FIG. 1.

Additionally the device 2 as shown in FIGS. 18 and 19 can be used with a shielding system 74 to prevent damage to the lung membranes. Such a shielding system 74 can be thin flexible wave dampening plate adapted to dampen the wave propagation to the lungs. Alternatively, air filled or high damping, reflecting materials including cellular polyurethane foam with a thin film skin or covering might be used.

The shock wave device preferably can be packaged in a sterile wrap or package and opened and connected in the operating room by the technical staff.

Figure 6:
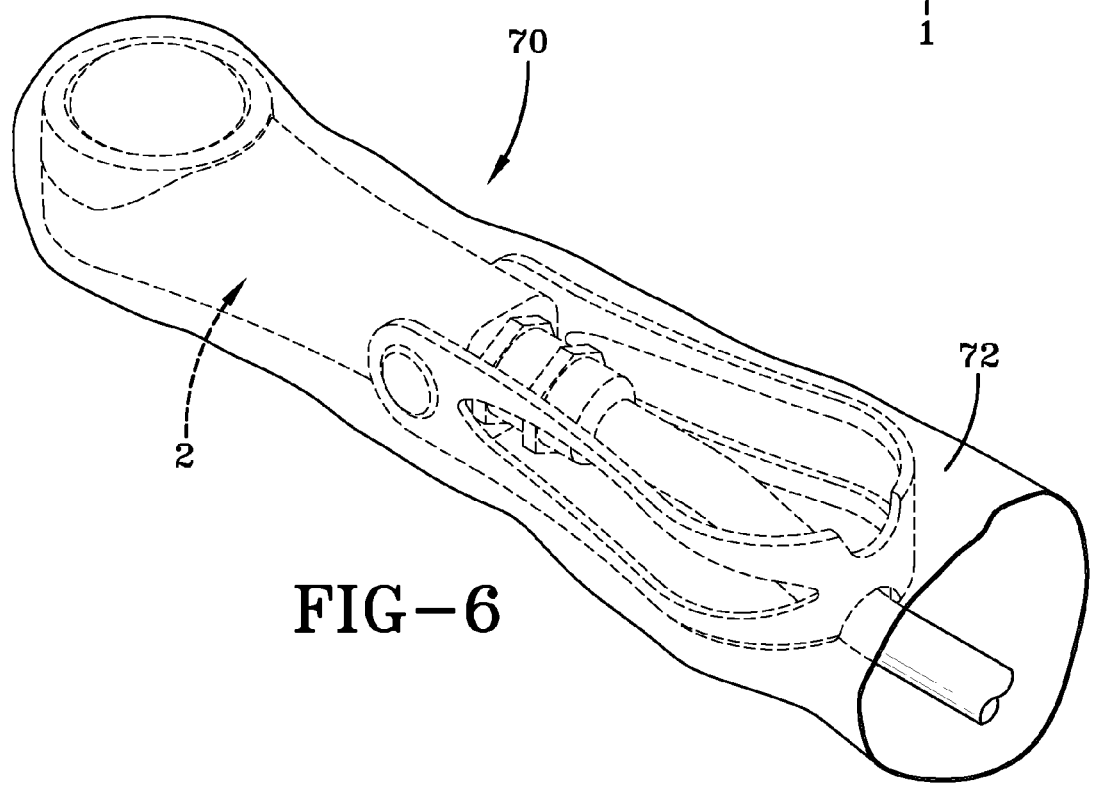
FIG. 6 is a perspective view of a sterile prophylactic sleeve for use with the applicator.

Alternatively as shown in FIG. 6 the device can be covered by a sterile prophylactic covering 70 of synthetic material similar to a latex or plastic glove. Some of these are already in use for other type of equipment which is used in the operating procedure of the open surgery. Preferably the covering has a long tube like portion 72 with a closed end and an open end into which the applicator 2 and a portion of the cabling 1 can be slid into. This sterile covering 70 being thin and flexible would not interfere with the wave transmission or the pivotable use of the handle 5. Shock wave transmission between the membrane and the sleeve as well between the sleeve and the tissue has to be achieved by sterile fluid medium like NACL solution or sterile ultrasound gel or other substances with coupling properties.

Figure 22:
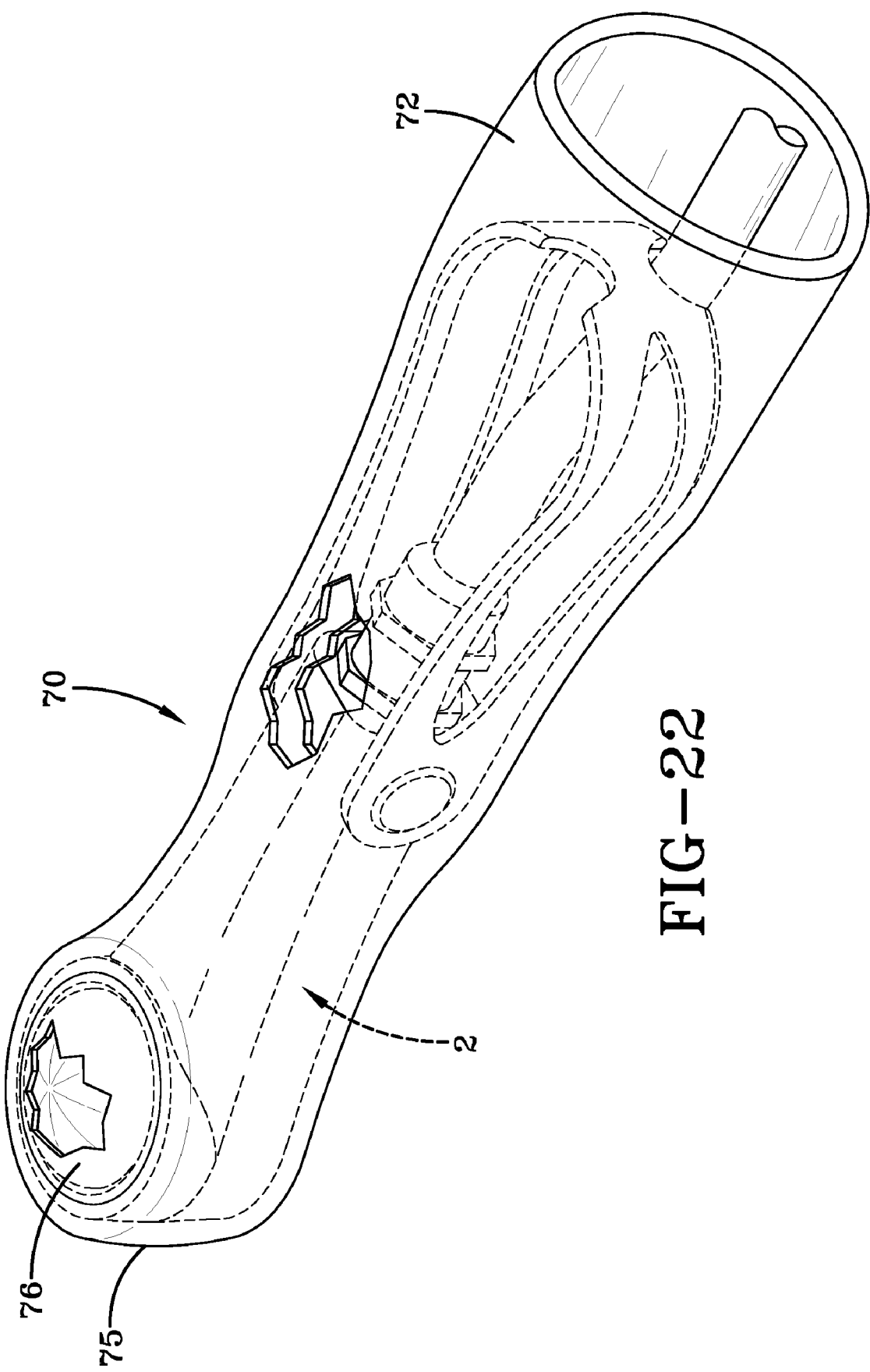
FIG. 22 is a view of a sterile applicator sleeve or cover with an integral shielding means.

As shown in FIG. 22 the sleeve 70 may include an integral shield 75 formed by an air filled double layer membrane or other wave dampening material such that the area above the reflector 15 or transmission zone directly under the outer membrane 3 is a single layer 76 not shielded, but other areas such as the back and sides of the device are shielded. Alternatively a simple shield 80 may be used that is a wave damping sterile pad or layer positioned between a sterile device 2 and the underlying lungs (not shown) above the heart.

Figure 21:
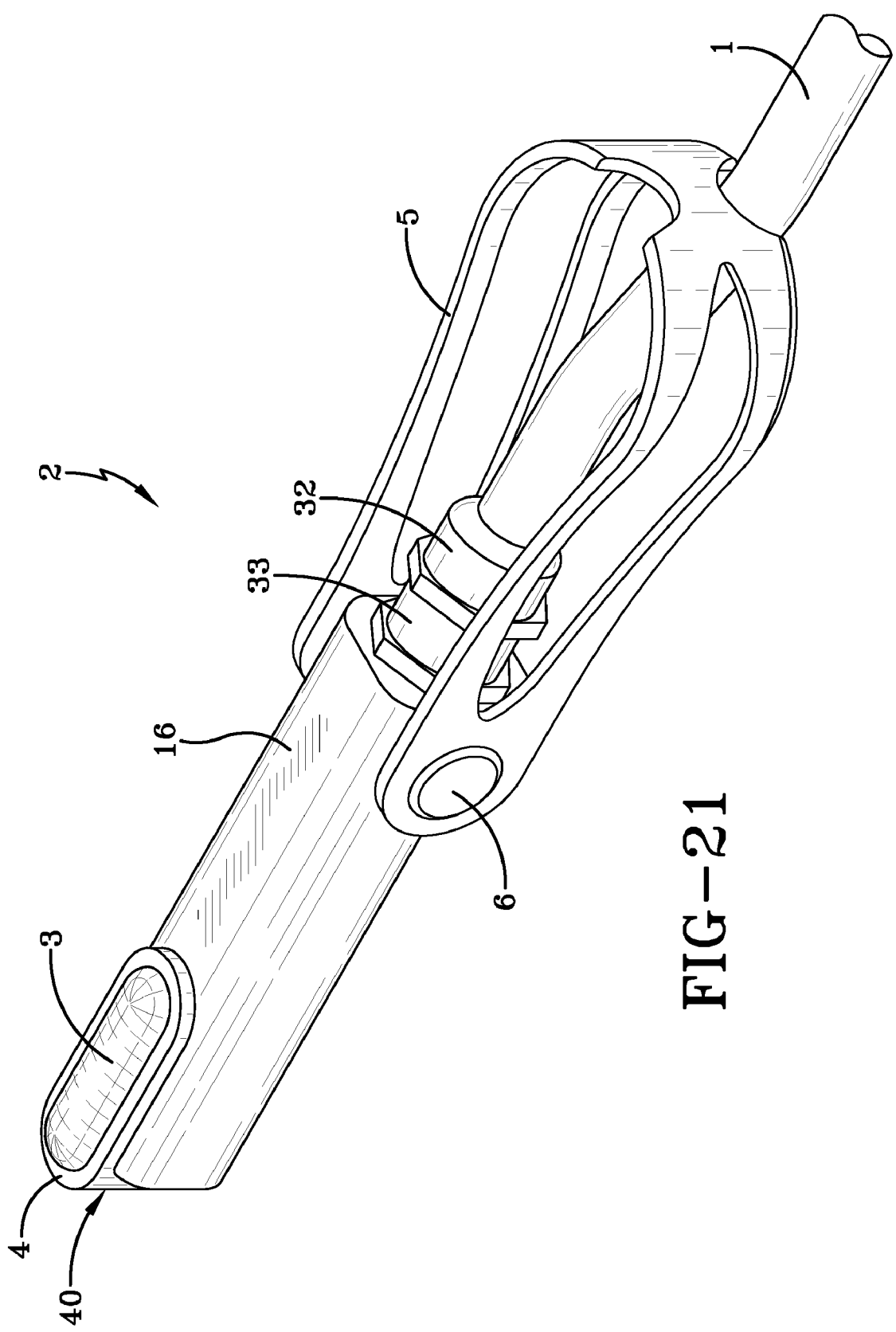
FIG. 21 is an alternative embodiment employing an ellipsoidal applicator head.

With reference to FIGS. 3 and 4 the reflector 15 it has the internal cavity 30 shown as a generalized paraboloid with a very divergent wave to stimulate the infarct tissue of a heart directly at the applicator exit or membrane 3 while only having a low pressure amplitude when being transmitted through the heart tissue which potentially might enter into the lung tissue. Alternatively, as shown in FIG. 21 the applicator device 2 can be made with an elliptical head portion 40, the reflector cavity 30 might be an ellipsoid with its focal point about 1-2 cm after the aperture. This will make possible that the heart wall will be behind the focal point (F2 geometrical) and the divergent beam of the shock wave is treating the tissue. The lung on the other side of the heart will be in the already low pressure because of the divergent shock wave amplitude (pressure). This is the case when the distance to the focal point is very big. In an unfocused spherical wave the pressure is lowered according to 1/distance2 and such a wave form can be emitted using the applicator device 2.

These and other aspects of the reflector characteristics and the use of the shock wave head have been described in co-pending application U.S. Ser. No. 11/238,731 portions of which are restated for a clear understanding of the method and use of the inventive device described above.

In the shock wave method of treating an organ of a mammal be it human or an animal with an at least partially exposed target site on the organ, the organ is positioned in a convenient orientation to permit the source of the emitted waves to most directly send the waves unobstructed to the target site to initiate shock wave stimulation of the target area with minimal, preferably no interfering tissue or bone features in the path of the emitting source or lens or membrane 3. Assuming the target area is within a projected area of the wave transmission, a single transmission dosage of wave energy may be used. The transmission dosage can be from a few seconds to 20 minutes or more dependent on the condition. The number of shock waves could be from 10 to a few hundred or a few thousand within one treatment. The repletion frequency of shock waves per second could be from 0.5-20 per second. Preferably the waves are generated from an unfocused or focused source. Preferably the shock waves should be emitted at maximum energy densities of about 0.3 $mJ/mm^2$ or less. The unfocused waves can be divergent or near planar and having a low pressure amplitude and density in the range of 0.00001 $mJ/mm^2$ to 0.3 $mJ/mm^2$ or less, most typically below 0.2 $mJ/mm^2$. The focused source preferably can use a diffusing lens or have a far-sight focus to minimize if not eliminate having the localized focus point within the tissue. Preferably the focused shock waves are used at a similarly effective low energy transmission or alternatively can be at higher energy but wherein the tissue target site is disposed pre-convergence inward of the geometric focal point of the emitted wave transmission.

These shock wave energy transmissions are effective in stimulating a cellular response and can be accomplished without creating the cavitation bubbles in the tissue of the target site. This effectively insures the organ does not have to experience the sensation of hemorrhaging so common in the higher energy focused wave forms having a focal point at or within the targeted treatment site.

If the target site is an organ subjected to a surgical procedure exposing at least some if not all of the organ within the body cavity the target site may be such that the patient or the portable shock wave applicator device 2 must be reoriented relative to the site and a second, third or more treatment dosage can be administered. The fact that the dosage is at a low energy the common problem of localized hemorrhaging is reduced making it more practical to administer multiple dosages of waves from various orientations to further optimize the treatment and cellular stimulation of the target site. Heretofore focused high energy multiple treatments induced pain and discomfort to the patient. The use of low energy focused or un-focused waves at the target site enables multiple sequential treatments.

The present method does not rely on precise site location per se. The physician's general understanding of the anatomy of the patient should be sufficient to locate the target area to be treated. This is particularly true when the exposed organ is visually within the surgeon's line of sight and this permits the lens or membrane 3 of the emitting shock wave applicator 2 to impinge on the organ tissue directly during the shockwave treatment. The treated area can withstand a far greater number of shock waves based on the selected energy level being emitted. For example at very low energy levels the stimulation exposure can be provided over prolonged periods as much as 20 minutes if so desired. The number of shock waves could be from 10 to a few hundred or a few thousand within one treatment. The repletion frequency of shock waves per second could be from 0.5-20 per second. At higher energy levels the treatment duration can be shortened to less than a minute, less than a second if so desired. The limiting factor in the selected treatment dosage is avoidance or minimization of cell hemorrhaging and other kinds of damage to the cells or tissue while still providing a stimulating stem cell activation or a cellular release or activation of VEGF and other growth factors.

The underlying principle of these shock wave therapy methods is to stimulate the body's own natural healing capability. This is accomplished by deploying shock waves to stimulate strong cells in the tissue to activate a variety of responses. The acoustic shock waves transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly not only can the energy intensity be reduced but also the number of applied shock wave impulses can be lowered from several thousand to as few as one or more pulses and still yield a beneficial stimulating response.

The use of shock waves as described above appears to involve factors such as thermal heating, light emission, electromagnetic field exposure, chemical releases in the cells as well as a microbiological response within the cells. Which combination of these factors plays a role in stimulating healing is not yet resolved. However, there appears to be a commonality in the fact that growth factors are released which applicants find indicative that otherwise dormant cells within the tissue appear to be activated which leads to the remarkable ability of the targeted organ or tissue to generate new growth or to regenerate weakened vascular networks in for example the cardio vascular system.

The use of shock wave therapy requires a fundamental understanding of focused and unfocused shock waves, coupled with a more accurate biological or molecular Focused shock waves are focused using ellipsoidal reflectors in electromechanical sources from a cylindrical surface or by the use of concave or convex lenses. Piezoelectric sources often use spherical surfaces to emit acoustic pressure waves which are self focused and have also been used in spherical electromagnetic devices.

The biological model proposed by co-inventor Wolfgang Schaden provides a whole array of clinically significant uses of shock wave therapy.

Accepting the biological model as promoted by W. Schaden, the peak pressure and the energy density of the shock waves can be lowered dramatically. Activation of the body's healing mechanisms will be seen by in growth of new blood vessels and the release of growth factors.

The biological model motivated the design of sources with low pressure amplitudes and energy densities. First: spherical waves generated between two tips 11, 13 of an electrode; and second: nearly even waves generated by generalized parabolic reflectors. Third: divergent shock front characteristics are generated by an ellipsoid behind F2. Unfocused sources are preferably designed for extended two dimensional areas/volumes like skin. The unfocused sources can provide a divergent wave pattern or a nearly planar wave pattern and can be used in isolation or in combination with focused wave patterns yielding to an improved therapeutic treatment capability that is non-invasive with few if any disadvantageous contraindications. Alternatively a focused wave emitting treatment may be used wherein the focal point extends preferably beyond the target treatment site, potentially external to the patient. This results in the reduction of or elimination of a localized intensity zone with associated noticeable pain effect while providing a wide or enlarged treatment volume at a variety of depths more closely associated with high energy focused wave treatment. The utilization of a diffuser type lens or a shifted far-sighted focal point for the ellipsoidal reflector enables the spreading of the wave energy to effectively create a convergent but off target focal point. This insures less tissue trauma while insuring cellular stimulation to enhance the healing process.

This method of treatment has the steps of, locating a treatment site, generating either convergent diffused or far-sighted focused shock waves or unfocused shock waves, of directing these shock waves to the treatment site; and applying a sufficient number of these shock waves to induce activation of one or more growth factors thereby inducing or accelerating healing.

The unfocused shock waves can be of a divergent wave pattern or near planar pattern preferably of a low peak pressure amplitude and density. Typically the energy density values range as low as 0.000001 $mJ/mm^2$ and having a high end energy density of below 1.0 $mJ/mm^2$, preferably 0.20 $mJ/mm^2$ or less. The peak pressure amplitude of the positive part of the cycle should be above 1.0 and its duration is below 1-3 microseconds.

The treatment depth can vary from the surface to the full depth of the treated organ. The treatment site can be defined by a much larger treatment area than the 0.10-3.0 $cm^2$ commonly produced by focused waves. The above methodology is particularly well suited for surface as well as sub-surface soft tissue organ treatments.

The above methodology is valuable in generation of tissue, vascularization and may be used in combination with stem cell therapies as well as regeneration of tissue and vascularization.

The methodology is useful in (re)vascularization of the heart, brain, liver, kidney and skin.

The methodology is useful in stimulating enforcement of defense mechanisms in tissue cells to fight infections from bacteria and can be used germicidally to treat or cleanse wounds or other target sites.

Conditions caused by cirrhosis of the liver can be treated by reversing this degenerative condition.

The implications of using the (re)generative features of this type of shock wave therapy are any weakened organ or tissue even bone can be strengthened to the point of reducing or eliminating the risk of irreparable damage or failure.

The stimulation of growth factors and activation of healing acceleration is particularly valuable to elderly patients and other high risk factor subjects.

Similar gains are visualized in organ transplant and complete organ regeneration, wherein a heart, liver, kidney, portions of the brain or any other organ or portions thereof of a human or animal may be transplanted into a patient, the organ being exposed to shock waves either prior to or after being transplanted.

Figure 7:
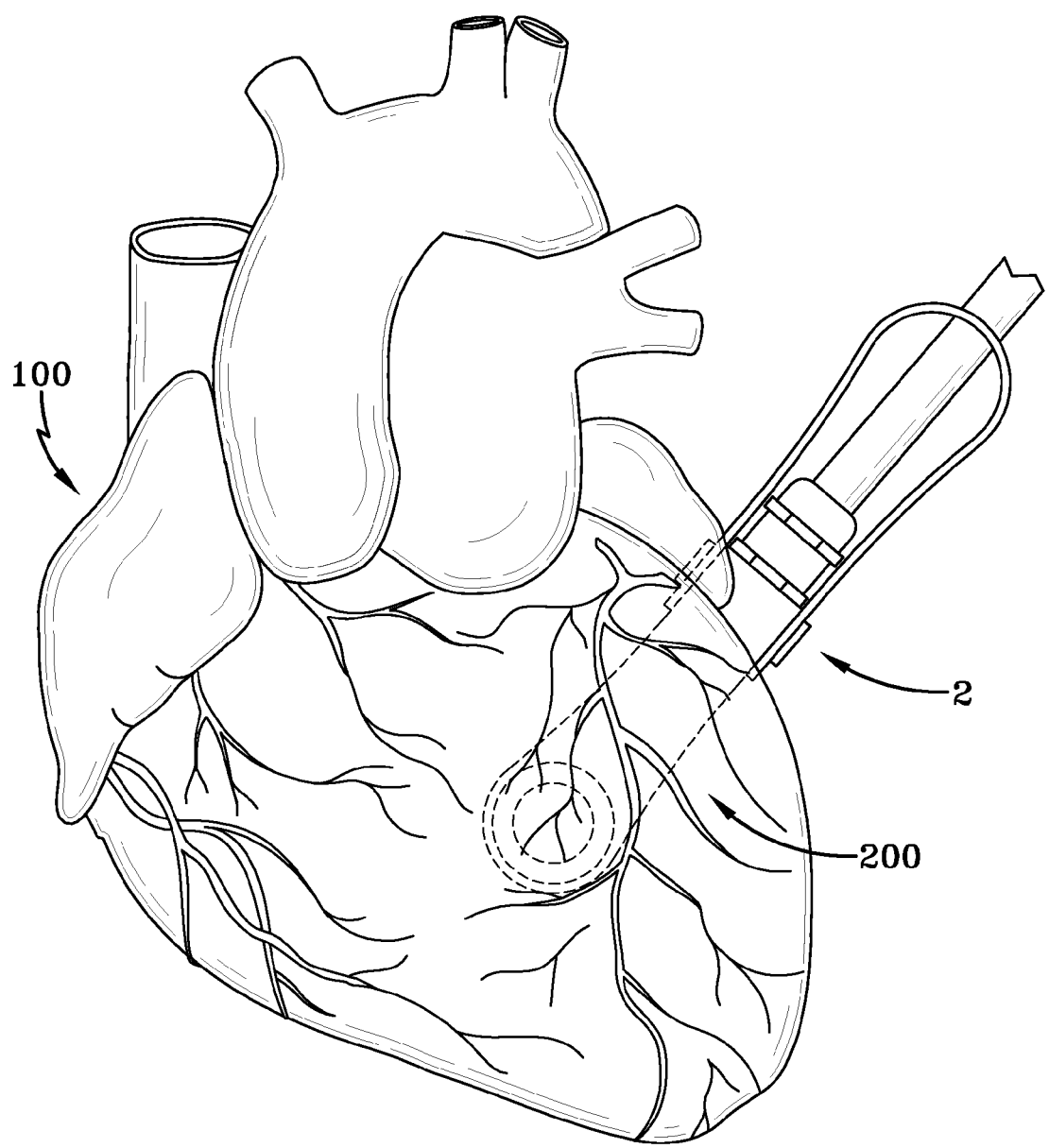
FIG. 7 is a perspective view of a frontal region of a heart being shock wave treated by a shock wave head according to the method of the present invention.
Figure 8:
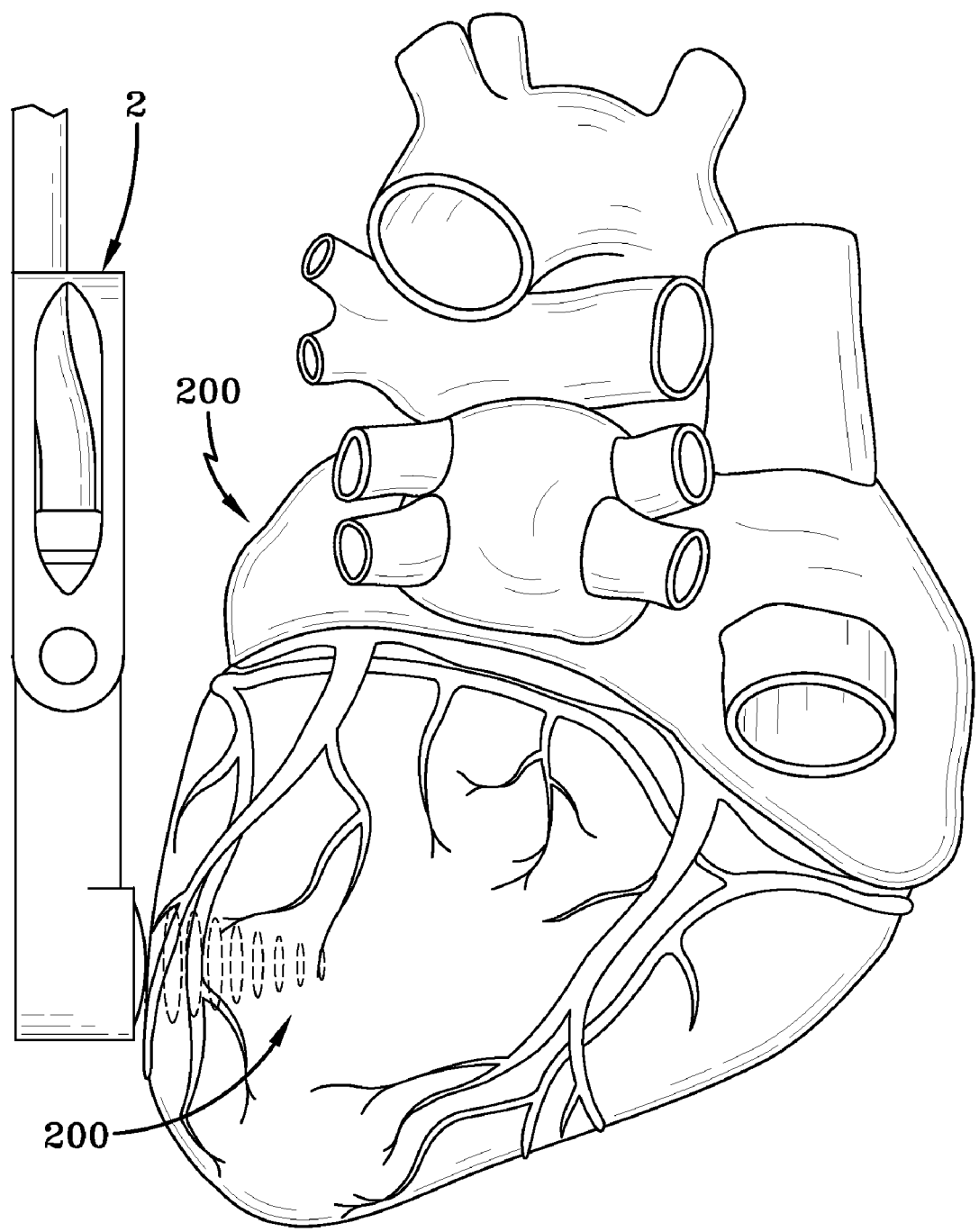
FIG. 8 is a perspective view of the posterior region of a heart being shock wave treated according to the present inventive method.
Figure 12:
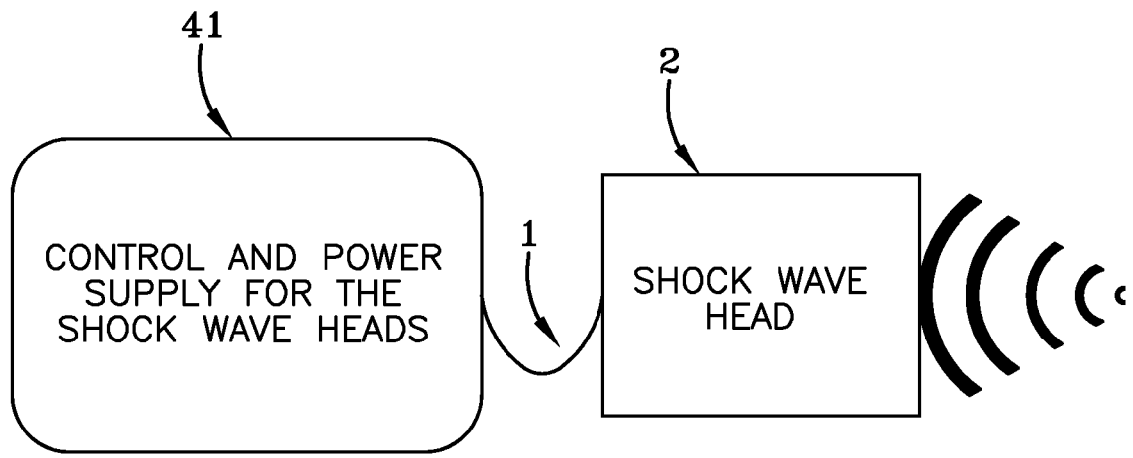
FIG. 12 is a schematic view of a shock wave system according to the present invention.

With reference to FIGS. 7 and 8 the organ 100 shown is a heart. In FIG. 7 a frontal view of the heart is shown wherein the frontal region is being bombarded with exemplary shock waves 200 wherein the shockwave applicator 2 is shown unobstructed to the tissue of the heart. The shockwave applicator 2 is connected through the cable 1 back to a control and power supply 41, as shown in FIG. 12. As illustrated the exemplary shock waves 200 emanate through the tissue of the heart providing a beneficial regenerating and revascularization capability that heretofore was unachieved. The beneficial aspects of the present methodology are that the heart 100 as shown fully exposed in the views FIGS. 13 and 14 can be partially exposed or have an access portal such that the shock wave head 2 can be inserted therein and directed to contact or be in near contact to the heart tissue is such a way that the admitted exemplary shock waves 200 can most directly and in the most unobstructed way be transmitted to the region needing treatment. The heart itself can be lifted in the myocardial cavity and the applicator 2 positioned beneath the heart and firing the wave pattern upwardly into the tissue as shown in FIG. 8. While the use of the shock wave applicator 2 in this fashion is clearly invasive it also has the beneficial aspects of providing a direct treatment to the cardiovascular area in need of regenerative or revascularization enhancement.

Figure 9:
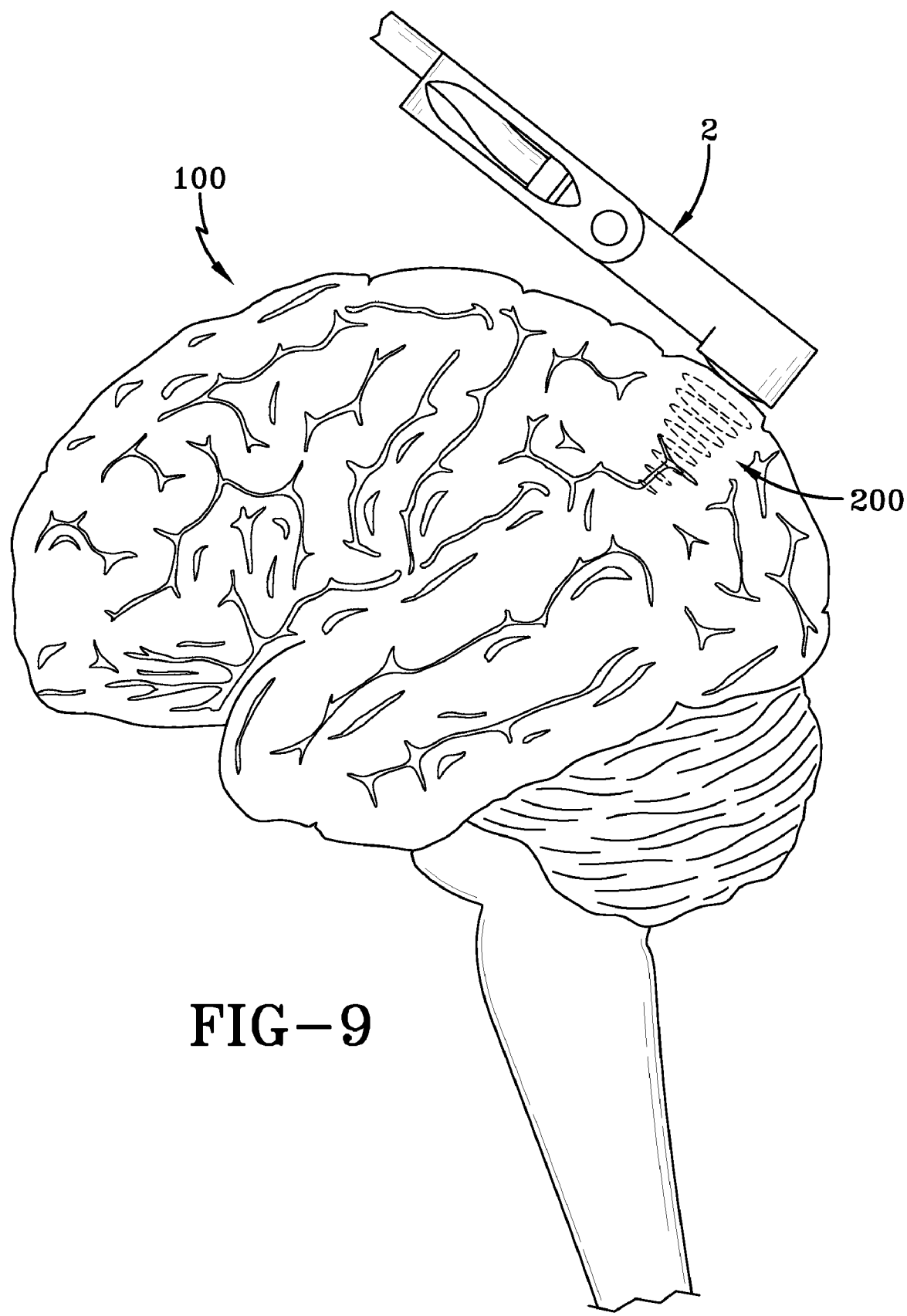
FIG. 9 is a perspective view of a brain being shock wave treated according to the method of the present invention.

With reference to FIG. 9, the organ 100 is a brain. As shown the brain and brain stem are completely exposed, however, normally only a small portion of the cranial cavity would be open such that the shockwave applicator 2 can be inserted therein to provide therapeutic shock wave treatments preferably of very low amplitude for stimulating certain regions of the brain for regenerative purposes.

Figure 10:
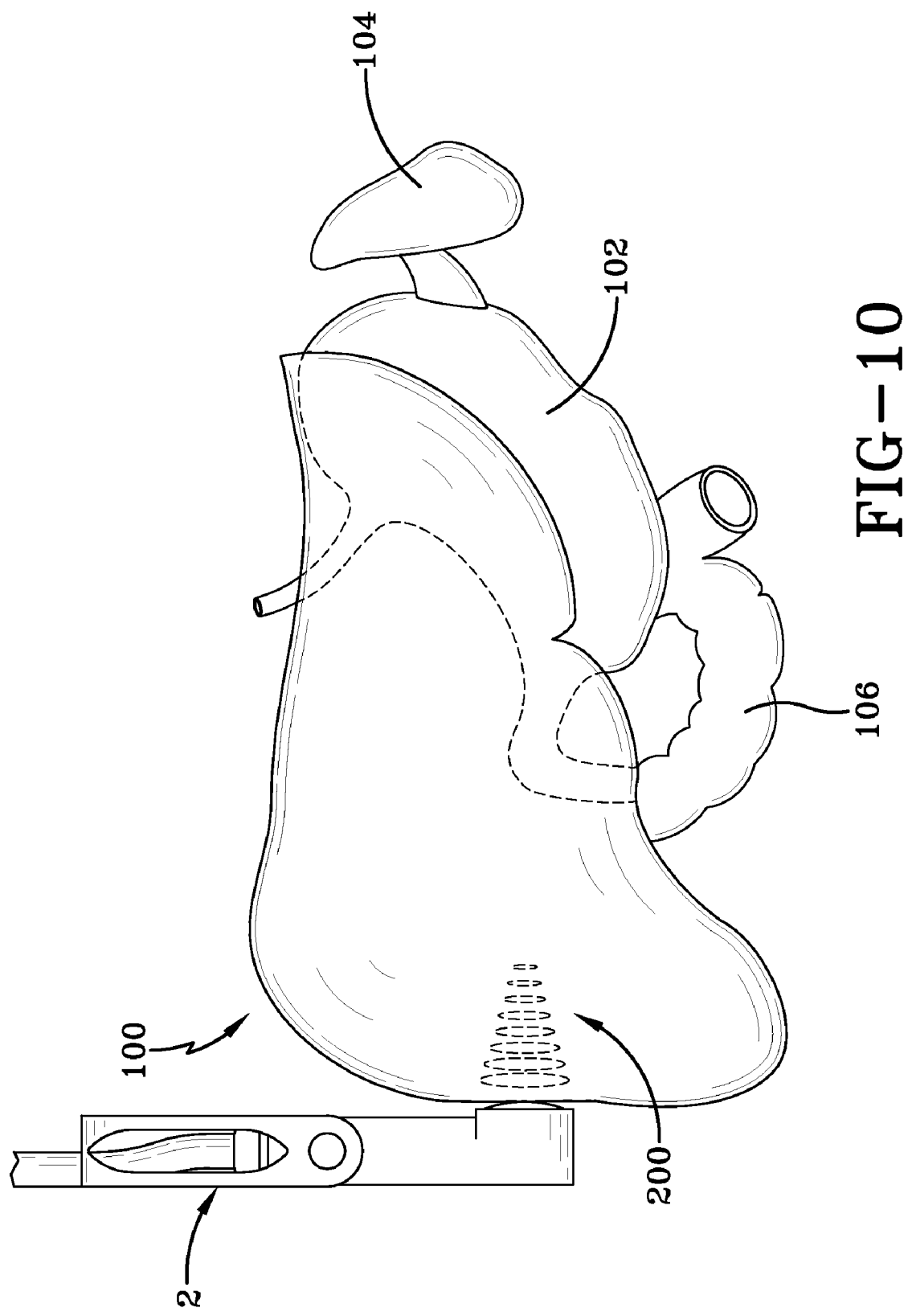
FIG. 10 is a perspective view of a liver being shock wave treated according to the method of the present invention.

In FIG. 10 a liver 100 is shown. In addition to the liver 100, the stomach 102, spleen 104 and duodenum 106 are also shown. The shock wave applicator 2 is in contact with the liver 100 and is providing a therapeutic shock wave treatment as illustrated wherein the exemplary shock waves 200 are being transmitted through the tissue of the liver. It is believed that the use of such exemplary shock waves 200 can help in enhancing liver regeneration particularly those that have been degenerative and in conditions that might be prone to failure. Again the liver 100 is shown fully exposed, however, in normal procedure only an access portal or opening may be needed such that the shock wave applicator 2 can be inserted there through and provide a direct unobstructed path to deliver shockwave treatments to this organ as well.

Figure 11:
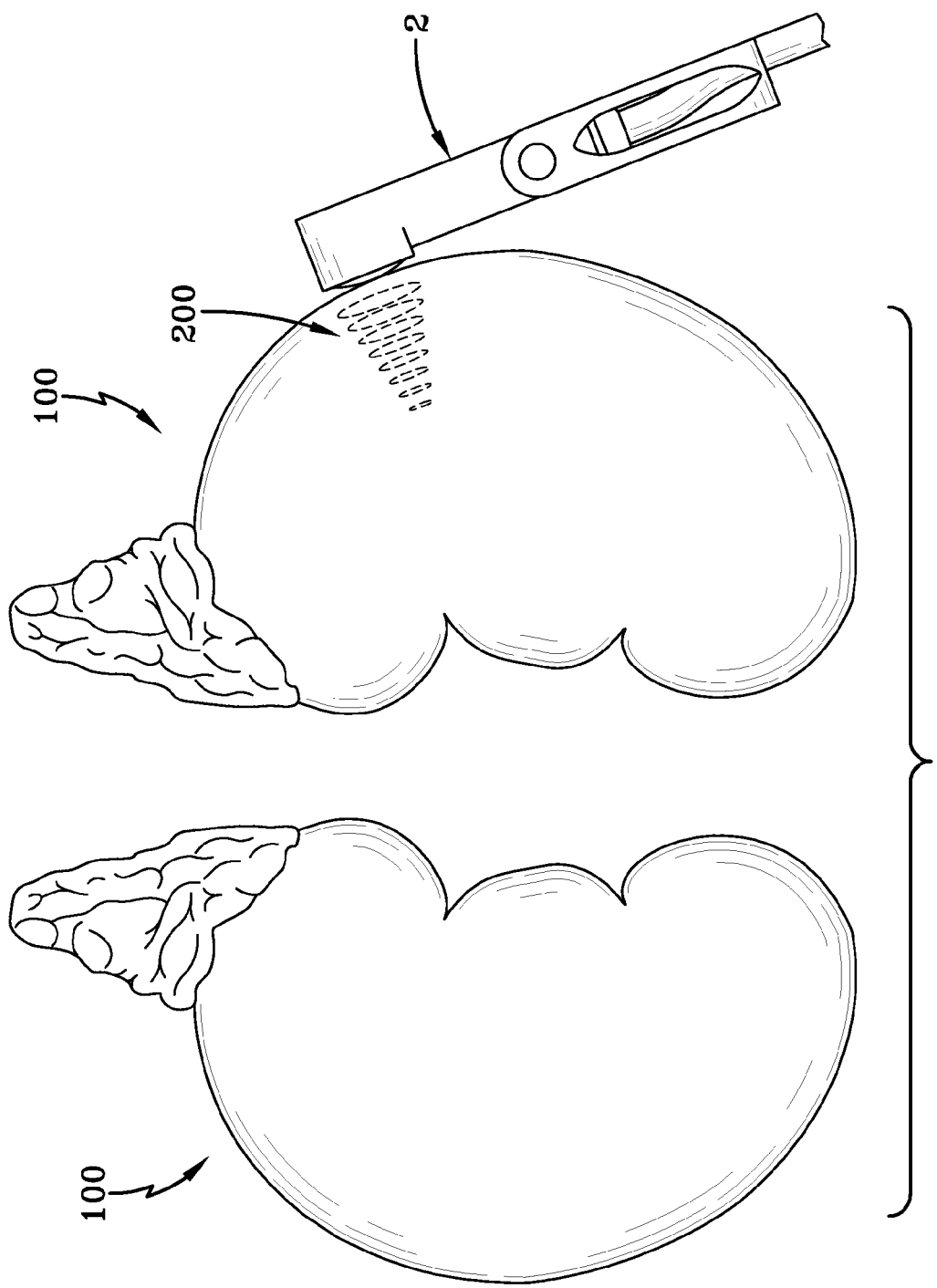
FIG. 11 is a perspective view of a pair of kidneys, one of said kidneys being shown treated by shock wave from shock wave head according to the method of the present invention.

In FIG. 11 a pair of kidneys 100 is shown as the organ 100 being treated. In this fashion the kidneys similar to the liver, brain or heart can be treated such that the shock wave applicator 2 can be in direct or near contact in an unobstructed path to admit shock waves 200 to this organ. This has the added benefit of generating maximum therapy to the afflicted organ in such a way that the healing process can be stimulated more directly. Again in each of these procedures as shown there is an invasive technique requiring the shock wave applicator 2 to enter either an access portal or an opening wherein the organ 100 is at least partially exposed to the exemplary shock waves 200 as can either be accomplished by a surgical procedure or any other means that would permit entry of the shock wave applicator 2 to the afflicted organ.

In each of the representative treatments as shown in FIGS. 7 through 11 the shockwave applicator 2 when used within a sterile sleeve or covering 70 as shown in FIG. 6 or 22 may simply be disinfected using a suitable antimicrobial disinfecting agent prior to use. Alternatively the applicator 2 may be sterilized when used without a sterile sleeve. As shown the sleeves or coverings 70 are preferably disposable and should be discarded after use. When treating any tissue or organ 100 the sterile sleeve 70 holding the applicator 2 or in the case of using the applicator 2 without a sleeve the tissue contacting surface should be coupled acoustically by using known means such as sterile fluids or viscous gels like ultrasound gels or even NaCl solutions to couple the transmitted shock wave into the organ in an aseptic sterile fashion.

In FIGS. 7-11 exemplary shock waves 200 are illustrated, it must be appreciated that any of the recognized shock wave patterns exhibited in FIGS. 13-17 can be used in the shock wave treatment of the various organs 100.

Heretofore such invasive techniques were not used in combination with shock wave therapy primarily because the shockwaves were believed to be able to sufficiently pass through interfering body tissue to achieve the desired result in a non-invasive fashion. While this may be true, in many cases if the degenerative process is such that an operation is required then the combination of an operation in conjunction with shockwave therapy only enhances the therapeutic values and the healing process of the patient and the organ such that regenerative conditions can be achieved that would include not only revascularization of the heart or other organs wherein sufficient or insufficient blood flow is occurring but also to enhance the improvement of ischemic tissue that may be occupying a portion of the organ. This ischemic tissue can then be minimized by the regenerative process of using shock wave therapy in the fashion described above to permit the tissue to rebuild itself in the region that has been afflicted.

As used throughout this application wherein the use of exemplary shock waves 200 in an unobstructed path has been described unobstructed path means that there is no or substantially no interfering tissue or bone skeletal mass between the shock wave applicator 2 and the treated organ. It is believed that the elimination of such interfering masses greatly enhances the control and the efficiency of the emitted exemplary shock waves 200 to create the desired beneficial healing effects and regenerative process needed for the organ to be repaired.

Furthermore such acoustic shock wave forms can be used in combination with drugs, chemical treatments, irradiation therapy or even physical therapy and when so combined the stimulated cells will more rapidly assist the body's natural healing response.

The present invention provides an apparatus for an effective treatment of indications, which benefit from low energy pressure pulse/shock waves having nearly plane or even divergent characteristics. With an unfocused wave having nearly plane wave characteristic or even divergent wave characteristics, the energy density of the wave may be or may be adjusted to be so low that side effects including pain are very minor or even do not exist at all.

In certain embodiments, the apparatus of the present invention is able to produce waves having energy density values that are below 0.3 mJ/mm2 or even as low as 0.000 001 mJ/mm2. In a preferred embodiment, those low end values range between 0.1-0.001 mJ/mm2. With these low energy densities, side effects are reduced and the dose application is much more uniform. Additionally, the possibility of harming surface tissue is reduced when using an apparatus of the present invention that generates waves having nearly plane or divergent characteristics and larger transmission areas compared to apparatuses using a focused shock wave source that need to be moved around to cover the affected area. The apparatus of the present invention also may allow the user to make more precise energy density adjustments than an apparatus generating only focused shock waves, which is generally limited in terms of lowering the energy output.

The treatment of the above mentioned indications are believed to be a first time use of acoustic shock wave therapy invasively. None of the work done to date has treated the above mentioned indications with convergent, divergent, planar or near-planar acoustic shock waves of low energy or focused shock waves in a direct unobstructed path from the emitting source lens or cover using the soft fluid filled organ as a transmitting medium directly. As is the use of acoustic shock waves for germicidal wound cleaning or preventive medical treatments.

With reference to FIGS. 13-17 the applicator 2 of the present invention can be provided with a reflector cavity 30 shaped or contoured to reflect the generated wave pattern 200 in a variety of shapes or geometric forms. In each of the following figures the wave pattern 200 includes a geometric pattern specific subset 200A through 200E.

Figure 13:
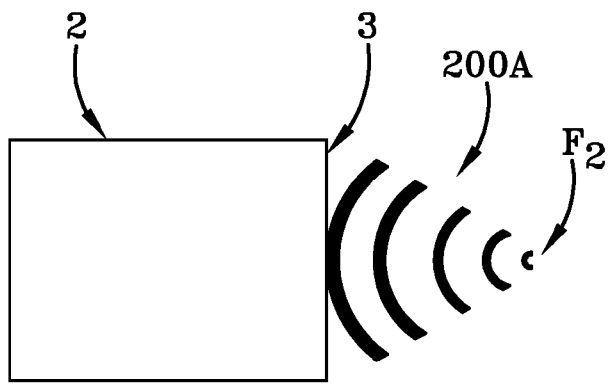
FIGS. 13-17 are illustrations of various shock wave patterns.

FIG. 13 is a simplified depiction of the pressure pulse/shock wave (PP/SW) generator, such as the shock wave applicator 2 showing focusing characteristics of transmitted acoustic pressure pattern 200A. The pattern as illustrated has waves that are converging as shown.

This converging wave pattern 200A is commonly used in focused shock wave treatments wherein the focal point $F_2$ is targeted at a specific point in the tissue mass 100. Alternatively the wave pattern can be used off target to avoid the high energy focal region if so desired. These wave patterns 200A are most commonly produced by using an ellipsoidal shaped reflector surface in the cavity 30.

Figure 14:
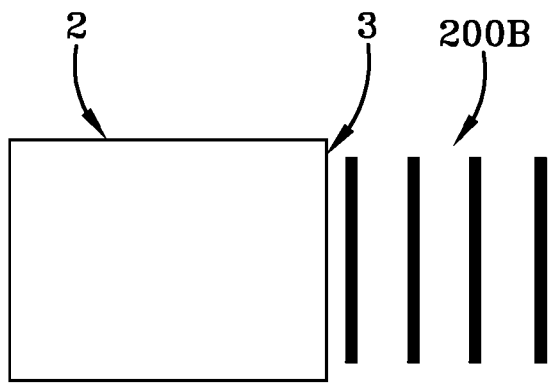

FIG. 14 is a simplified depiction of a pressure pulse/shock wave generator, such as a shock wave head, with plane wave characteristics. Numeral 2 indicates the position of a pressure pulse applicator 2 according to the present invention, which generates a pressure pulse wave pattern 200B which is leaving the housing at the membrane or lens position 3, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window or membrane 3.

Figure 15:
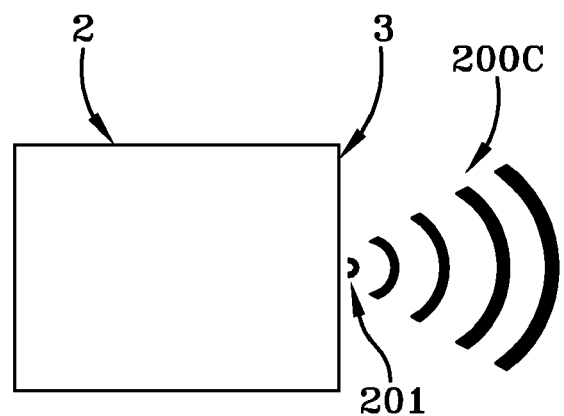

FIG. 15 is a simplified depiction of a pressure pulse shock wave generator (shock wave head) with divergent wave characteristics. The divergent wave fronts 200C may be leaving the exit window 3 at point 201 where the amplitude of the wave front is very high. This point 201 could be regarded as the source point for the pressure pulses 200C. In FIG. 1c the pressure pulse source may be a point source, that is, the pressure pulse may be generated by an electrical discharge of an electrode under water between electrode tips. However, the pressure pulse may also be generated, for example, by an explosion.

Figure 16:
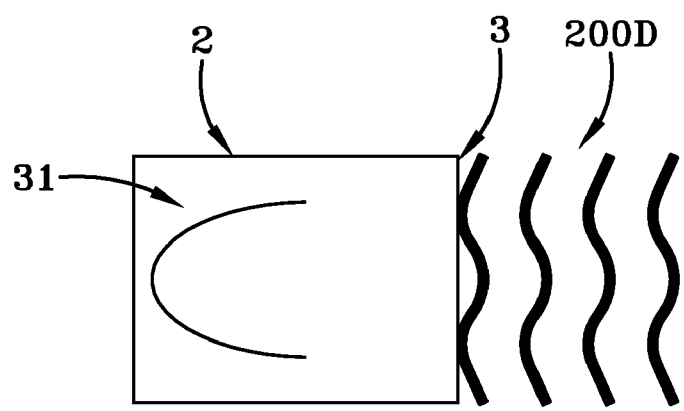

FIG. 16 is a simplified depiction of the pressure pulse/shock wave generator (shock wave head) having as a focusing element an paraboloid ($y^2=2px$). Thus, the characteristics of the wave fronts 200D generated behind the exit window 3 are disturbed plane ("parallel"), the disturbance resulting from phenomena ranging from electrode burn down, spark ignition spatial variation to diffraction effects. However, other phenomena might contribute to the disturbance. This is common in so called planar patterns.

Figure 17:
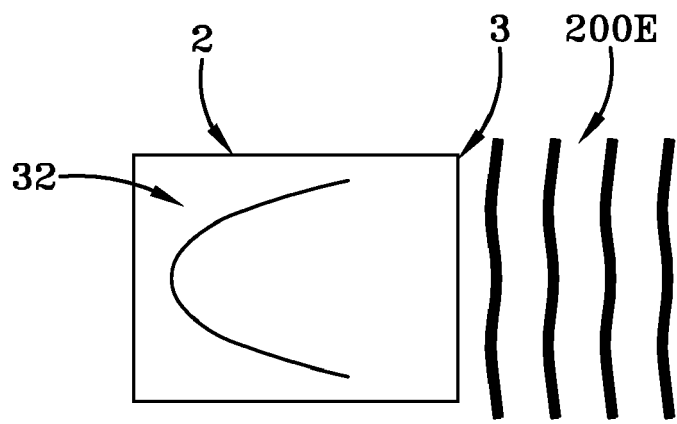

FIG. 17 is a simplified depiction of the pressure pulse/shock wave generator (shock wave head) having as a focusing element a generalized paraboloid ($y^n=2px$, with $1.2<n<2.8$ and $n \neq 2$). Thus, the characteristics of the wave fronts 200E generated behind the exit window or membrane 3 are, compared to the wave fronts generated by a paraboloid ($y^2=2px$), less disturbed, that is, nearly plane (or nearly parallel or nearly even). Thus, conformational adjustments of a regular paraboloid ($y^2=2px$) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid ($y^2=2px$) with p=1.25, introduction of a new electrode may result in p being about 1.05. If an electrode is used that adjusts itself to maintain the distance between the electrode tips ("adjustable electrode") and assuming that the electrodes burn down is 4 mm (z=4 mm), p will increase to about 1.45. To compensate for this burn down, and here the change of p, and to generate nearly plane wave fronts over the life span of an electrode, a generalized paraboloid having, for example n=1.66 or n=2.5 may be used. An adjustable electrode is, for example, disclosed in U.S. Pat. No. 6,217,531.

Various wave patterns 200A-200E are by no means intended to be more than exemplary and any such wave pattern or type may be used at the surgeon's discretion. Accordingly the depiction 200 in FIGS. 7-12 are intended to mean any style of wave pattern emitted including, but not limited to the subset 200A-200E.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A small portable hand-held electro-hydraulic shock wave applicator device comprising:
   an applicator housing extending longitudinally;
   a side firing shock wave applicator head at one end of the applicator housing;
   a pair of electrodes with tips to create a shock wave generating spark to create the shock waves being used in medical applications having amplitudes above 0.1 MPa and rise times of the amplitude below 100 ns, the duration of a shock wave being below 1-3 micro-seconds (µs) for the positive part of a cycle and above a micro-second for the negative part of a cycle;
   a reflector for redirecting and shaping a shock wave pattern transverse to a longitudinal axis of the shock wave device;
   a membrane or lens covering said reflector for transmitting said shock wave pattern; and wherein the pair of electrodes includes an inner electrode centered and held in an inner probe housing and at an opposite side of the applicator head is an outer electrode, the pair of electrodes being aligned and gapped at a distance S and being partially surrounded by the reflector wherein the shock waves are emitted from the applicator head in a sideways direction relative to the length of the applicator housing.

2. The shock wave applicator device of claim 1 wherein the reflector is a generalized paraboloid.

3. The shock wave applicator device of claim 1 wherein the reflector is a generalized paraboloid generating a very divergent wave emitted from the applicator.

4. The shock wave applicator device of claim 1 wherein the reflector is an ellipsoid.

5. The shock wave applicator device of claim 4 wherein the reflector is an ellipsoid having a focal point about 1-2 cm after the aperture.

6. The shock wave applicator device of claim 1 wherein the shock wave head further comprises:
a pivotable handle attached to the longitudinal housing for holding said device, the handle being pivotally inclined relative to the longitudinally extending housing of the device between 0° and at least 180°.

7. The shock wave applicator device of claim 1 wherein a space between said reflector and said membrane or lens defines a cavity, the two electrodes being located within said cavity.

8. The shock wave applicator device of claim 7 wherein the cavity is filled with a fluid medium.

9. The shock wave applicator device of claim 8 wherein said fluid medium is water under pressure.

10. The shock wave applicator device of claim 9 further comprises:
an inlet passageway and an outlet passageway in said reflector open to said cavity; and
an inlet fluid hose and an outlet fluid hose connected to said passageways for fluid delivery.

11. The shock wave applicator device of claim 7 wherein one of said electrodes is movably adjustable.

12. The shock wave applicator device of claim 7 wherein the device has the two electrodes with tips wherein the tips are fixed.

13. The method of employing a small portable hand-held shock wave applicator device comprises the steps of:
providing an at least partially exposed organ or direct access portal to an organ,
activating an acoustic shock wave generator or source to emit acoustic shock waves from a side firing applicator head with a pair of electrodes with tips to create a shock wave generating spark to create shock waves used in medical applications having amplitudes above 0.1 MPa and rise times of the amplitude below 100 ns, the duration of a shock wave being below 1-3 micro-seconds (μs) for the positive part of a cycle and above a micro-second for the negative part of a cycle, the shock wave emitted from a shock wave applicator head in a side firing pattern relative to the shock wave applicator device, a reflector for redirecting and shaping a shock wave pattern transverse to a longitudinal axis of the shock wave device; a membrane or lens covering said reflector for transmitting said shock wave pattern; and wherein the pair of electrodes includes an inner electrode centered and held in an inner probe housing and at an opposite side of the applicator head is an outer electrode, the pair of electrodes being aligned and gapped at a distance S and being partially surrounded by the reflector wherein the shock waves are emitted from the applicator head in a sideways direction relative to the length of the applicator housing; and
subjecting the organ to the acoustic shock waves stimulating said organ wherein the organ is positioned within an unobstructed path of the emitted shock waves, positioning the shock wave head adjacent to and on an inclination relative to the organ, and emitting a shock wave pattern in a generally transverse direction relative to the applicator head.

14. The method of claim 13 further comprises repositioning the shock wave head at a second position or inclination and generating a second shock wave emission.

15. The method of claim 14 includes the step of positioning the applicator by setting a holding means at an angle between 0° and 360° relative to the applicator head prior to emitting the shock waves, the holding means being a pivotable handle.

16. The method of claim 15 includes the step of positioning the applicator by setting the holding means at an angle between 0° and 180° relative to the applicator head prior to emitting the shock waves.

17. The method of claim 13 wherein the step of providing an at least partially exposed organ or direct access portal to an organ includes an open heart surgical procedure performed on a heart to be temporarily relieved of circulating function surgically open to inspection and shock wave treatment.

18. The method of claim 13 wherein the step of activating the shock wave generator or source to emit shock waves includes the step of controlling the emission of shock waves to be responsive to a repetitive body function.

19. The method of claim 18 wherein the step of controlling the emission of shock waves includes the step of using an ECG monitor to record the heartbeat pattern and QRS and T curve profile and triggering the emission of shock waves to the R portion of the curve representing the peak amplitude during a heart contraction.

20. The method of claim 19 further comprises the step of applying an acoustic coupling fluid medium onto the contacting surface of the membrane or lens cover of the device or the sleeve or both to couple the transmitted shock waves into the tissue or organ to be treated to couple the applicator with or without a sleeve covering to the tissue or organ.

* * * * *